(12) United States Patent
Brooks et al.

(10) Patent No.: US 12,070,557 B2
(45) Date of Patent: Aug. 27, 2024

(54) WRAP SYSTEMS FOR MEDICAL DEVICE KITS

(71) Applicant: C. R. Bard, Inc., Franklin Lakes, NJ (US)

(72) Inventors: Christopher K. Brooks, Lawrenceville, GA (US); Lyndsay Sweeney, Pine Lake, GA (US); Kelly J. Christian, Draper, UT (US); Jennifer Stryker, Minnetonka, MN (US); Matt Loui, North Salt Lake, UT (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 0 days.

(21) Appl. No.: 18/371,968

(22) Filed: Sep. 22, 2023

(65) Prior Publication Data

US 2024/0009423 A1  Jan. 11, 2024

Related U.S. Application Data

(63) Continuation of application No. 16/738,953, filed on Jan. 9, 2020, now Pat. No. 11,766,540, which is a
(Continued)

(51) Int. Cl.
*B65B 63/00* (2006.01)
*A61B 42/00* (2016.01)
(Continued)

(52) U.S. Cl.
CPC .......... *A61M 25/002* (2013.01); *A61B 42/00* (2016.02); *A61B 42/10* (2016.02); *A61B 46/00* (2016.02);
(Continued)

(58) Field of Classification Search
CPC ....... B65B 11/00; B65B 11/56; B65B 63/005; A61B 2050/3008; A61B 2050/314; A61B 2020/318
(Continued)

(56) References Cited

U.S. PATENT DOCUMENTS

| 2,172,455 | A | 9/1939 | Samuel |
| 2,265,680 | A | 12/1941 | Zella |

(Continued)

FOREIGN PATENT DOCUMENTS

| EP | 3055995 B1 | 6/2018 |
| GB | 836258 A | 6/1960 |

(Continued)

OTHER PUBLICATIONS

EP 14851523.2 filed Mar. 31, 2016 Extended European Search Report dated Apr. 5, 2017.
(Continued)

*Primary Examiner* — Valentin Neacsu
(74) *Attorney, Agent, or Firm* — Rutan & Tucker LLP

(57) ABSTRACT

Medical device kits for use in placing, maintaining, altering, and/or removing medical devices in, on, and/or from the body of a patient can include one or more wrap assemblies for use in the placement/maintenance procedure. The one or more wrap assemblies of the medical device kit can include various features to assist the clinician performing the particular procedure, such as a urinary catheterization procedure. A wrap assembly can include a wrap body including a front surface defining an aseptic field for the urinary catheterization procedure, a plurality of pockets on the front surface, and urinary catheterization components disposed in the plurality of pockets, the urinary catheterization components arranged in a predetermined order of use for the urinary catheterization procedure. The wrap assembly can
(Continued)

be in a rolled configuration. A method of using the wrap assembly includes unrolling the wrap assembly and removing the urinary catheterization components to perform the procedure.

8 Claims, 31 Drawing Sheets

Related U.S. Application Data continuation of application No. 15/701,152, filed on Sep. 11, 2017, now Pat. No. 10,537,707, which is a continuation-in-part of application No. 15/430,349, filed on Feb. 10, 2017, now Pat. No. 10,799,311.

(60) Provisional application No. 62/294,944, filed on Feb. 12, 2016.

(51) Int. Cl.
| | |
|---|---|
| *A61B 42/10* | (2016.01) |
| *A61B 46/00* | (2016.01) |
| *A61B 50/30* | (2016.01) |
| *A61M 25/00* | (2006.01) |
| *A61M 25/02* | (2006.01) |
| *B65B 11/00* | (2006.01) |
| *B65B 11/56* | (2006.01) |
| *B65D 65/22* | (2006.01) |
| *A61B 50/00* | (2016.01) |
| *A61M 5/158* | (2006.01) |

(52) U.S. Cl.
CPC ............ *A61B 50/30* (2016.02); *A61M 25/02* (2013.01); *B65B 11/00* (2013.01); *B65D 65/22* (2013.01); *A61B 2050/002* (2016.02); *A61B 2050/3008* (2016.02); *A61B 2050/314* (2016.02); *A61B 2050/318* (2016.02); *A61M 5/158* (2013.01); *A61M 2005/1586* (2013.01); *A61M 2025/0246* (2013.01); *A61M 2025/0253* (2013.01); *A61M 2025/0273* (2013.01); *A61M 2205/0205* (2013.01); *B65B 11/56* (2013.01); *B65B 63/005* (2013.01)

(58) Field of Classification Search
USPC ............................................. 53/425; 206/571
See application file for complete search history.

(56) References Cited

U.S. PATENT DOCUMENTS

| | | | |
|---|---|---|---|
| 2,733,113 A | 1/1956 | Humbargar | |
| 3,017,990 A | 1/1962 | Singerman | |
| 3,062,371 A * | 11/1962 | Patience | A61F 15/001 |
| | | | 206/440 |
| 3,095,088 A | 6/1963 | Blaikie et al. | |
| 3,119,495 A | 1/1964 | Pratt | |
| 3,137,387 A | 6/1964 | Alfred | |
| 3,162,307 A | 12/1964 | Regan, Jr. | |
| 3,318,510 A | 5/1967 | Quarles et al. | |
| 3,503,391 A | 3/1970 | Melges | |
| 3,650,393 A | 3/1972 | Reiss et al. | |
| 3,651,615 A * | 3/1972 | Bohner | B29C 65/7891 |
| | | | 493/203 |
| 3,749,233 A | 7/1973 | McCormick, Jr. | |
| 3,768,971 A | 10/1973 | Fishpaw | |
| 3,780,857 A * | 12/1973 | Rosano, Jr. | A61B 50/30 |
| | | | 206/370 |
| 3,791,382 A | 2/1974 | Collins | |
| 3,817,190 A | 6/1974 | Evangelista | |
| 3,884,412 A | 5/1975 | Price | |
| 3,952,738 A | 4/1976 | Krzewinski | |
| 4,051,845 A * | 10/1977 | Collins | A61B 46/23 |
| | | | 128/855 |
| 4,342,390 A * | 8/1982 | Mitchell | A61B 50/30 |
| | | | 206/363 |
| D268,811 S | 5/1983 | Black | |
| D271,422 S | 11/1983 | Breland | |
| 4,415,089 A | 11/1983 | Ruffa | |
| D272,600 S | 2/1984 | Kubas | |
| 4,466,659 A | 8/1984 | Carpentier et al. | |
| 4,476,860 A | 10/1984 | Collins et al. | |
| 4,522,302 A | 6/1985 | Paikoff | |
| 4,523,679 A | 6/1985 | Paikoff et al. | |
| D292,024 S | 9/1987 | Hanssen et al. | |
| 4,844,259 A | 7/1989 | Glowczewskie, Jr. et al. | |
| 5,022,521 A | 6/1991 | Kane | |
| 5,074,316 A | 12/1991 | Dowdy | |
| 5,082,111 A | 1/1992 | Corbitt, Jr. et al. | |
| D325,518 S | 4/1992 | Matkovich | |
| 5,203,457 A | 4/1993 | Garcia | |
| 5,749,842 A | 5/1998 | Cheong et al. | |
| 5,816,253 A | 10/1998 | Sosebee | |
| 5,879,620 A | 3/1999 | Cohen | |
| 5,931,303 A * | 8/1999 | Salvadori | A61M 25/002 |
| | | | 229/87.01 |
| 5,931,304 A | 8/1999 | Hammond | |
| 5,947,296 A | 9/1999 | Castora | |
| 6,016,915 A | 1/2000 | Almond | |
| 6,149,302 A | 11/2000 | Taheri | |
| 6,308,875 B1 | 10/2001 | Almo | |
| 6,412,639 B1 | 7/2002 | Hickey | |
| 6,436,085 B1 | 8/2002 | Lauer | |
| 6,460,702 B2 | 10/2002 | Hammond | |
| 6,595,361 B2 | 7/2003 | Sugama | |
| 6,837,027 B2 | 1/2005 | Hickey | |
| 6,957,738 B2 | 10/2005 | Hammond | |
| D540,665 S | 4/2007 | Gupta et al. | |
| 7,273,148 B2 * | 9/2007 | Perry | B25H 3/00 |
| | | | 206/214 |
| 7,293,654 B1 | 11/2007 | Wilson, Jr. et al. | |
| 7,331,463 B2 | 2/2008 | Hickey | |
| D589,347 S | 3/2009 | Dacey | |
| 7,624,869 B2 | 12/2009 | Primer | |
| 7,628,275 B2 | 12/2009 | Smith | |
| D609,819 S | 2/2010 | Tomes et al. | |
| 7,673,754 B2 | 3/2010 | Wilson, Jr. et al. | |
| D623,765 S | 9/2010 | Tomes et al. | |
| 7,798,323 B1 * | 9/2010 | McCann | A61F 17/00 |
| | | | 206/370 |
| D636,894 S | 4/2011 | Tomes et al. | |
| 7,967,139 B2 | 6/2011 | Brinker | |
| D650,912 S | 12/2011 | Tomes et al. | |
| D657,124 S | 4/2012 | Dacey et al. | |
| 8,167,130 B2 * | 5/2012 | Holstein | A61F 17/00 |
| | | | 206/499 |
| 8,240,471 B2 | 8/2012 | Brinker | |
| 8,261,963 B2 | 9/2012 | Gaynor et al. | |
| 8,302,775 B2 | 11/2012 | Holstein | |
| 8,448,786 B2 | 5/2013 | Tomes et al. | |
| 8,464,722 B2 | 6/2013 | Chua | |
| 8,485,419 B2 | 7/2013 | Gaynor et al. | |
| 8,631,935 B2 | 1/2014 | Tomes et al. | |
| 8,678,190 B2 | 3/2014 | Tomes et al. | |
| 8,685,189 B2 * | 4/2014 | Pamperin | B32B 37/182 |
| | | | 156/267 |
| D704,856 S | 5/2014 | Tomes et al. | |
| 8,727,957 B2 * | 5/2014 | Smith | A61B 50/00 |
| | | | 493/405 |
| 8,746,452 B2 | 6/2014 | Tomes et al. | |
| 8,789,702 B1 | 7/2014 | Shingyouchi-Hall | |
| 8,852,502 B2 | 10/2014 | Andgrebe et al. | |
| 8,875,940 B2 | 11/2014 | Danchisin et al. | |
| 9,162,781 B2 | 10/2015 | Lien | |
| 9,174,782 B2 | 11/2015 | Gaynor et al. | |
| 9,254,176 B2 | 2/2016 | Hartley | |
| D752,452 S | 3/2016 | Kearns et al. | |
| 9,283,352 B2 | 3/2016 | Tomes et al. | |
| 9,296,535 B2 | 3/2016 | Gaynor et al. | |
| 9,327,042 B2 | 5/2016 | Griesbach, III et al. | |

(56) References Cited

U.S. PATENT DOCUMENTS

| | | | |
|---|---|---|---|
| D764,943 S | 8/2016 | Murray et al. | |
| 9,522,753 B2 | 12/2016 | Tomes et al. | |
| 9,693,756 B2 | 7/2017 | Tomes et al. | |
| 9,745,088 B2 | 8/2017 | Tomes et al. | |
| 9,795,761 B2 | 10/2017 | Lockwood et al. | |
| 9,808,400 B2 | 11/2017 | Tomes et al. | |
| 9,808,596 B2 | 11/2017 | Tomes et al. | |
| 9,872,969 B2 | 1/2018 | Conway et al. | |
| 10,413,700 B2 | 9/2019 | Wiley et al. | |
| 10,537,707 B2* | 1/2020 | Brooks | A61M 25/02 |
| 10,639,120 B2 | 5/2020 | Turturro et al. | |
| 10,799,311 B2* | 10/2020 | Loui | A61F 17/00 |
| 11,389,257 B2* | 7/2022 | Loui | A61B 50/30 |
| 11,766,540 B2* | 9/2023 | Brooks | A61B 42/10 53/425 |
| 11,931,125 B2* | 3/2024 | Johnson | A61F 17/00 |
| 2002/0088729 A1 | 7/2002 | Urbanski | |
| 2004/0031721 A1* | 2/2004 | Mann | A61B 10/04 206/570 |
| 2004/0158186 A1 | 8/2004 | Hall | |
| 2004/0256283 A1 | 12/2004 | Jasper et al. | |
| 2005/0211590 A1 | 9/2005 | McClure et al. | |
| 2005/0224392 A1* | 10/2005 | Perry | B25H 3/00 206/214 |
| 2005/0268573 A1* | 12/2005 | Yan | A61L 2/26 206/439 |
| 2006/0206992 A1 | 9/2006 | Godshaw et al. | |
| 2006/0231443 A1 | 10/2006 | Jonasson et al. | |
| 2007/0161971 A1* | 7/2007 | House | A61M 25/002 206/364 |
| 2007/0260166 A1 | 11/2007 | Johnson | |
| 2008/0007706 A1 | 1/2008 | Reisinger et al. | |
| 2008/0120945 A1 | 5/2008 | Holbrook et al. | |
| 2008/0249476 A1* | 10/2008 | Bierman | A61M 25/00 604/174 |
| 2008/0283426 A1 | 11/2008 | Primer et al. | |
| 2009/0230000 A1 | 9/2009 | Sackos | |
| 2009/0236259 A1 | 9/2009 | Hicks | |
| 2010/0218462 A1* | 9/2010 | Murray | B29C 66/72341 53/456 |
| 2010/0274205 A1 | 10/2010 | Morelli et al. | |
| 2010/0307941 A1 | 12/2010 | Tomes et al. | |
| 2010/0307942 A1 | 12/2010 | Tomes et al. | |
| 2010/0311026 A1 | 12/2010 | Tomes et al. | |
| 2011/0232234 A1 | 9/2011 | Lockwood et al. | |
| 2011/0233079 A1 | 9/2011 | Macinnes et al. | |
| 2011/0284012 A1 | 11/2011 | McCollough | |
| 2011/0284410 A1 | 11/2011 | Lockwood | |
| 2011/0290260 A1 | 12/2011 | Tomes et al. | |
| 2011/0290262 A1 | 12/2011 | Tomes et al. | |
| 2012/0065566 A1 | 3/2012 | Bar-Natan | |
| 2012/0145589 A1 | 6/2012 | Macinnes et al. | |
| 2012/0150123 A1 | 6/2012 | Lawrence et al. | |
| 2012/0168334 A1 | 7/2012 | Wittrock | |
| 2012/0202000 A1 | 8/2012 | Bricker et al. | |
| 2012/0222686 A1 | 9/2012 | Lockwood et al. | |
| 2012/0298114 A1 | 11/2012 | Landsman et al. | |
| 2012/0318706 A1 | 12/2012 | Holstein | |
| 2012/0325704 A1 | 12/2012 | Kerns et al. | |
| 2013/0037440 A1 | 2/2013 | Danchisin et al. | |
| 2013/0056011 A1 | 3/2013 | Taub et al. | |
| 2013/0081355 A1 | 4/2013 | Gaynor et al. | |
| 2013/0092724 A1 | 4/2013 | Gaynor et al. | |
| 2013/0111852 A1 | 5/2013 | Farmer et al. | |
| 2013/0112589 A1* | 5/2013 | Lien | A61M 1/69 493/240 |
| 2013/0152946 A1 | 6/2013 | Sosnowski | |
| 2013/0269713 A1 | 10/2013 | Bui et al. | |
| 2013/0277248 A1 | 10/2013 | Tomes et al. | |
| 2014/0021087 A1 | 1/2014 | Adler et al. | |
| 2014/0119677 A1* | 5/2014 | Lerner | B65B 43/267 493/227 |
| 2014/0138269 A1 | 5/2014 | Ghosh | |
| 2014/0142465 A1 | 5/2014 | Tomes et al. | |
| 2014/0231287 A1 | 8/2014 | Tomes et al. | |
| 2014/0231288 A1 | 8/2014 | Tomes et al. | |
| 2014/0257250 A1 | 9/2014 | Palmer | |
| 2014/0262851 A1 | 9/2014 | Adler et al. | |
| 2014/0272873 A1 | 9/2014 | Svensson et al. | |
| 2014/0353189 A1 | 12/2014 | Lotosky-Compton | |
| 2015/0027922 A1 | 1/2015 | Fresco | |
| 2015/0033673 A1 | 2/2015 | Lien | |
| 2015/0034521 A1 | 2/2015 | Lien | |
| 2015/0048103 A1 | 2/2015 | Danchisin et al. | |
| 2015/0053582 A1* | 2/2015 | Lloyd | B65D 33/01 206/363 |
| 2015/0083627 A1 | 3/2015 | Gorman | |
| 2015/0101616 A1* | 4/2015 | Wiley | A61B 50/20 53/492 |
| 2015/0217919 A1* | 8/2015 | Varbanov | B65D 75/20 229/125.22 |
| 2015/0238351 A1 | 8/2015 | Tsimbler | |
| 2015/0258304 A1 | 9/2015 | Tomes et al. | |
| 2015/0266649 A1 | 9/2015 | Sweeney | |
| 2015/0327934 A1 | 11/2015 | Thomas et al. | |
| 2015/0335855 A1 | 11/2015 | Tomes et al. | |
| 2015/0367011 A1 | 12/2015 | Kalmon et al. | |
| 2015/0374729 A1* | 12/2015 | Glauber | A61K 31/045 206/572 |
| 2016/0016718 A1 | 1/2016 | Berbert et al. | |
| 2016/0022853 A1 | 1/2016 | Hajime et al. | |
| 2016/0031606 A1* | 2/2016 | Ktytor | B25H 3/00 383/39 |
| 2016/0095663 A1 | 4/2016 | Richart | |
| 2016/0135895 A1 | 5/2016 | Faasse et al. | |
| 2016/0166800 A1 | 6/2016 | Tomes et al. | |
| 2016/0167871 A1 | 6/2016 | Nickell | |
| 2016/0187309 A1 | 6/2016 | Kang et al. | |
| 2016/0193444 A1 | 7/2016 | Tomes et al. | |
| 2016/0271283 A1 | 9/2016 | Kozin | |
| 2017/0216556 A1* | 8/2017 | Bierman | A61M 25/02 |
| 2017/0216558 A1 | 8/2017 | Hughett et al. | |
| 2017/0232226 A1* | 8/2017 | Loui | A61F 13/00051 206/571 |
| 2017/0275582 A1* | 9/2017 | Bendis | A61B 10/0283 |
| 2017/0296282 A1 | 10/2017 | Turturro et al. | |
| 2017/0296283 A1 | 10/2017 | Turturro et al. | |
| 2017/0296284 A1 | 10/2017 | Turturro et al. | |
| 2017/0319183 A1 | 11/2017 | Tomes et al. | |
| 2017/0368302 A1* | 12/2017 | Brooks | A61B 46/00 |
| 2020/0147341 A1* | 5/2020 | Brooks | A61M 25/002 |
| 2021/0015577 A1* | 1/2021 | Loui | A61B 50/30 |
| 2022/0346900 A1 | 11/2022 | Johnson | A61B 46/00 |
| 2024/0009423 A1* | 1/2024 | Brooks | B65B 11/00 |

FOREIGN PATENT DOCUMENTS

| | | |
|---|---|---|
| GB | 2396550 A | 6/2004 |
| WO | 9506449 A1 | 3/1995 |
| WO | 2010128554 A1 | 11/2010 |
| WO | 2011025486 A1 | 3/2011 |
| WO | 2011131953 A1 | 10/2011 |
| WO | 2013120182 A1 | 8/2013 |
| WO | 2015054660 A2 | 4/2015 |
| WO | 2016033089 A1 | 3/2016 |
| WO | 20170139680 A1 | 8/2017 |

OTHER PUBLICATIONS

EP 14851523.2 filed Mar. 31, 2016 Intent to Grant dated Feb. 26, 2018.

PCT/US14/60172 filed Oct. 10, 2014 International Search Report and Written Opinion dated Mar. 25, 2015.

PCT/US2017/017528 filed Feb. 10, 2017 International Search Report and Written Opinion dated Jun. 21, 2017.

PCT/US2018/050473 filed Sep. 11, 2018 International Search Report and Written Opinion dated Nov. 28, 2018.

Thompson, H; "Optimizing Package Design for EtO Sterilization"; 12,35 https://web.archive.org/web/20160112004508/http://www.mddionline.com/article/optimizing-package-design-eto-steriliza-

(56) References Cited

OTHER PUBLICATIONS tion; Jan. 12, 2006 (downloaded from the World Wide Web, Jun. 6, 2017]; figure; 1st paragraph.

U.S. Appl. No. 14/512,235, filed Oct. 10, 2014 Advisory Action dated Jun. 22, 2017.

U.S. Appl. No. 14/512,235, filed Oct. 10, 2014 Final Office Action dated Apr. 4, 2017.

U.S. Appl. No. 14/512,235, filed Oct. 10, 2014 Final Office Action dated Jul. 25, 2018.

U.S. Appl. No. 14/512,235, filed Oct. 10, 2014 Non-Final Office Action dated Jan. 7, 2019.

U.S. Appl. No. 14/512,235, filed Oct. 10, 2014 Non-Final Office Action dated Nov. 1, 2017.

U.S. Appl. No. 14/512,235, filed Oct. 10, 2014 Notice of Allowance dated May 15, 2019.

U.S. Appl. No. 14/512,235, filed Oct. 10, 2014 Notice of Panel Decision dated Aug. 1, 2017.

U.S. Appl. No. 14/512,235, filed Oct. 10, 2014 Non-Final Office Action dated Sep. 9, 2016.

U.S. Appl. No. 15/430,349, filed Feb. 10, 2017 Advisory Action dated Apr. 26, 2019.

U.S. Appl. No. 15/430,349, filed Feb. 10, 2017 Advisory Action dated Jan. 2, 2020.

U.S. Appl. No. 15/430,349, filed Feb. 10, 2017 Final Office Action dated Feb. 21, 2019.

U.S. Appl. No. 15/430,349, filed Feb. 10, 2017 Final Office Action dated Oct. 29, 2019.

U.S. Appl. No. 15/430,349, filed Feb. 10, 2017 Non-Final Office Action dated May 18, 2020.

U.S. Appl. No. 15/430,349, filed Feb. 10, 2017 Non-Final Office Action dated May 31, 2019.

U.S. Appl. No. 15/430,349, filed Feb. 10, 2017 Non-Final Office Action dated Sep. 14, 2018.

U.S. Appl. No. 15/430,349, filed Feb. 10, 2017 Restriction Requirement dated Jul. 12, 2018.

U.S. Appl. No. 15/701,152, filed Sep. 11, 2017 Final Office Action dated Jul. 9, 2019.

U.S. Appl. No. 15/701,152, filed Sep. 11, 2017 Non-Final Office Action dated Feb. 8, 2019.

U.S. Appl. No. 15/701,152, filed Sep. 11, 2017 Restriction Requirement dated Oct. 1, 2018.

U.S. Appl. No. 16/738,953, filed Jan. 9, 2020 Board Decision dated Mar. 23, 2023.

U.S. Appl. No. 16/738,953, filed Jan. 9, 2020 Examiner's Answer dated Jun. 9, 2022.

U.S. Appl. No. 16/738,953, filed Jan. 9, 2020 Final Office Action dated Sep. 9, 2021.

U.S. Appl. No. 16/738,953, filed Jan. 9, 2020 Non-Final Office Action dated May 7, 2021.

U.S. Appl. No. 16/738,953, filed Jan. 9, 2020 Notice of Allowance dated May 24, 2023.

U.S. Appl. No. 17/556,907, filed Dec. 20, 2021 Restriction Requirement dated May 12, 2023.

U.S. Appl. No. 17/866,980, filed Jul. 18, 2022 Final Office Action dated Aug. 16, 2023.

U.S. Appl. No. 17/866,980, filed Jul. 18, 2022 Non-Final Office Action dated Feb. 15, 2023.

U.S. Appl. No. 17/866,980, filed Jul. 18, 2022 Restriction Requirement dated Nov. 28, 2022.

U.S. Appl. No. 17/063,451, filed Oct. 5, 2020 Non-Final Office Action dated Nov. 3, 2021.

U.S. Appl. No. 17/063,451, filed Oct. 5, 2020 Notice of Allowance dated May 3, 2022.

\* cited by examiner

WRAP SYSTEMS FOR MEDICAL DEVICE KITS

CROSS-REFERENCE TO RELATED APPLICATIONS

This application is a continuation of U.S. patent application Ser. No. 16/738,953, filed Jan. 9, 2020, now U.S. Pat. No. 11,766,540, which is a continuation of U.S. patent application Ser. No. 15/701,152, filed Sep. 11, 2017, now U.S. Pat. No. 10,537,707, which is a continuation-in-part of U.S. patent application Ser. No. 15/430,349, filed Feb. 10, 2017, now U.S. Pat. No. 10,799,311, titled "Wrap Systems for Medical Device Kits," which claims the benefit of U.S. Provisional Patent Application No. 62/294,944, filed Feb. 12, 2016, titled "Wrap Systems for Medical Device Kits," each of which is hereby incorporated by reference herein in its entirety.

BRIEF SUMMARY

Briefly summarized, embodiments of the present invention are directed to medical device kits for use in placing, maintaining, altering, and/or removing medical devices in, on, and/or from the body of a patient or user. Such medical device kits can include one or more wrap assemblies for the placing, maintaining, altering, and/or removing of medical devices.

In some embodiments, for example, a medical device is provided including one or more wrap assemblies can include various features to assist the clinician or user performing a medical procedure. Any one or more of the wrap assemblies comprises a rollable or foldable wrap body that includes a front surface, wherein the front surface is configured to define at least an aseptic field. A plurality of pockets is included on the front surface of the wrap body. The pockets are configured to contain therein a plurality of medical components. The medical components are arranged in the pockets in a predetermined order of use for the medical procedure. Instructions are provided on the front surface of the wrap body for the medical procedure. Folded edges can be included on the wrap body to prevent the components from slipping off the wrap body and to facilitate grasping of the wrap body by a clinician or user without compromising the aseptic field.

In some embodiments, for example, a urinary catheterization kit is provided including a wrap body having a front surface, a plurality of pockets on the front surface, and instructions on the front surface for using the urinary catheterization kit. The front surface of the wrap body is configured to define at least an aseptic field. The pockets on the front surface of the wrap body are configured to contain a plurality of urinary catheterization components. The catheterization components are arranged in the pockets in a predetermined order of use for a urinary catheterization procedure.

In such embodiments, the wrap body is configured to roll up around the catheterization components.

In such embodiments, the pockets are formed by one or more pieces of wrap-body material welded to the wrap body by ultrasonic welds defining bottoms and sides of the pockets.

In such embodiments, the catheterization components are selected from one or more pairs of gloves, an underpad, one or more perineal wipes, hand sanitizer, lubricant, an antiseptic, swab sticks, a urinary catheter, drainage tubing, a drainage bag, and a specimen container.

In such embodiments, the catheterization components include at least a drainage bag. The catheterization kit is configured for placement of the drainage bag over the pockets to sandwich at least some other catheterization components between the drainage bag and the wrap body. A combination of the drainage bag and the wrap body are configured to roll up around the at least some other catheterization components.

In such embodiments, the catheterization components further include at least a specimen container. The catheterization kit is configured for placement of the specimen container over the drainage bag when the drainage bag is placed over the pockets to sandwich the at least some other catheterization components between the drainage bag and the wrap body. The combination of the drainage bag and the wrap body are configured to roll up around the specimen container. In other words, the catheterization kit is configured for placement of the specimen container in a center of a combined roll of the drainage bag and the wrap body.

In such embodiments, the instructions are presented on the front surface of the wrap body. The instructions are presented in accordance with the catheterization components arranged in the pockets of the wrap body in the predetermined order of use, which provides a stepwise system for the urinary catheterization procedure.

In some embodiments, for example, a urinary catheterization kit is provided including a wrap body of a sterilizable material including a front surface, a plurality of pockets on the front surface, and instructions printed on the front surface, the pockets, or a combination thereof. The front surface of the wrap body is configured to provide at least an aseptic field. The pockets on the front surface of the wrap body include an arrangement of catheterization components including at least an intermittent catheter. The instructions printed on the front surface of the wrap body, the pockets, or the combination thereof are presented in a predetermined order together with the arrangement of catheterization components, which provides a stepwise system for a urinary catheterization procedure with the intermittent catheter.

In such embodiments, removal of at least some of the catheterization components from the pockets reveals instructions hidden by the at least some of the catheterization components prior to their removal. The instructions revealed by the removal of the at least some of the catheterization components are further part of the stepwise system for the urinary catheterization procedure.

In such embodiments, the pockets are formed by one or more pieces of the sterilizable material adhered or ultrasonically welded to the wrap body. Adhesive beads or ultrasonic welds respectively define bottoms and sides of the pockets.

In such embodiments, the catheterization components further include one or more catheterization components selected from one or more pairs of gloves, an underpad, one or more perineal wipes, hand sanitizer, lubricant, an antiseptic, swab sticks, drainage tubing, a drainage bag, and a specimen container.

In such embodiments, the wrap body is configured to roll up around the catheterization components.

In such embodiments, the catheterization components further include at least a drainage bag. The catheterization kit is configured for placement of the drainage bag over the pockets to sandwich at least some other catheterization components between the drainage bag and the wrap body. The combination of the drainage bag and the wrap body are configured to roll up around the at least some other catheterization components.

In such embodiments, the catheterization components further include at least a specimen container. The catheterization kit is configured for placement of the specimen container over the drainage bag when the drainage bag is placed over the pockets to sandwich at the least some other catheterization components between the drainage bag and the wrap body. The combination of the drainage bag and the wrap body are configured to roll up around the specimen container. In other words, the catheterization kit is configured for placement of the specimen container in a center of a combined roll of the drainage bag and the wrap body.

In some embodiments, for example, a method is provided including forming a wrap body including a front surface for a urinary catheterization kit; forming a plurality of pockets on the front surface; printing instructions on the front surface, the pockets, or a combination thereof; and filling the pockets with the catheterization components. Forming the wrap body includes forming the wrap body from a sterilizable material. Forming the plurality of pockets includes configuring the pockets to contain an arrangement of catheterization components for a urinary catheterization procedure. Printing the instructions includes presenting the instructions on the front surface of the wrap body, the pockets, or a combination thereof in a predetermined order according to a stepwise system for the urinary catheterization procedure. Filling the pockets with the catheterization components includes filling the pockets for subsequent removal of the catheterization components according to the stepwise system for the urinary catheterization procedure.

In such embodiments, the method further comprises rolling the wrap body around the catheterization components to form the urinary catheterization kit.

In such embodiments, the method further comprises sterilizing the urinary catheterization kit. Sterilizing the urinary catheterization kit provides at least an aseptic field over the front surface of the wrap body upon unrolling the urinary catheterization kit.

In such embodiments, the method further comprises placing a drainage bag over the pockets to sandwich at least some other catheterization components in the pockets between the drainage bag and the wrap body. In addition, the method further comprises rolling a combination of the drainage bag and the wrap body around the at least some other catheterization components to form the urinary catheterization kit.

In such embodiments, the method further comprises placing a specimen container over the drainage bag. Rolling the combination of the drainage bag and the wrap body around the at least some other catheterization components includes rolling the combination of the drainage bag and the wrap body around the specimen container to form the urinary catheterization kit.

In such embodiments, forming the plurality of pockets on the front surface of the wrap body includes ultrasonically welding one or more pieces of the sterilizable material to the wrap body to form bottoms and sides of the pockets with ultrasonic welds.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician or user's hands when using the device to be described herein, while the word "distal" refers to a direction relatively further from the clinician or user's hands. For example, the end of a catheter (e.g., PICC (peripherally inserted central catheter), urinary catheter, etc.) placed within the body of a patient or user is considered a distal end of the catheter, while the catheter end remaining outside the body is a proximal end of the catheter. Also, the words "including," "has," and "having," as used herein, including the claims, shall have the same meaning as the word "comprising."

Embodiments of the present invention are generally directed to kits for use in placing, maintaining, altering, and/or removing medical devices in, on, and/or from the body of a patient. Such medical device kits can include one or more wrap assemblies for use in the placement/maintenance procedure. In accordance with present embodiments, the one or more wrap assemblies of the medical device kit can include various features to assist the clinician or user performing the particular procedure. These various features are outlined in further detail below.

Figure 1:
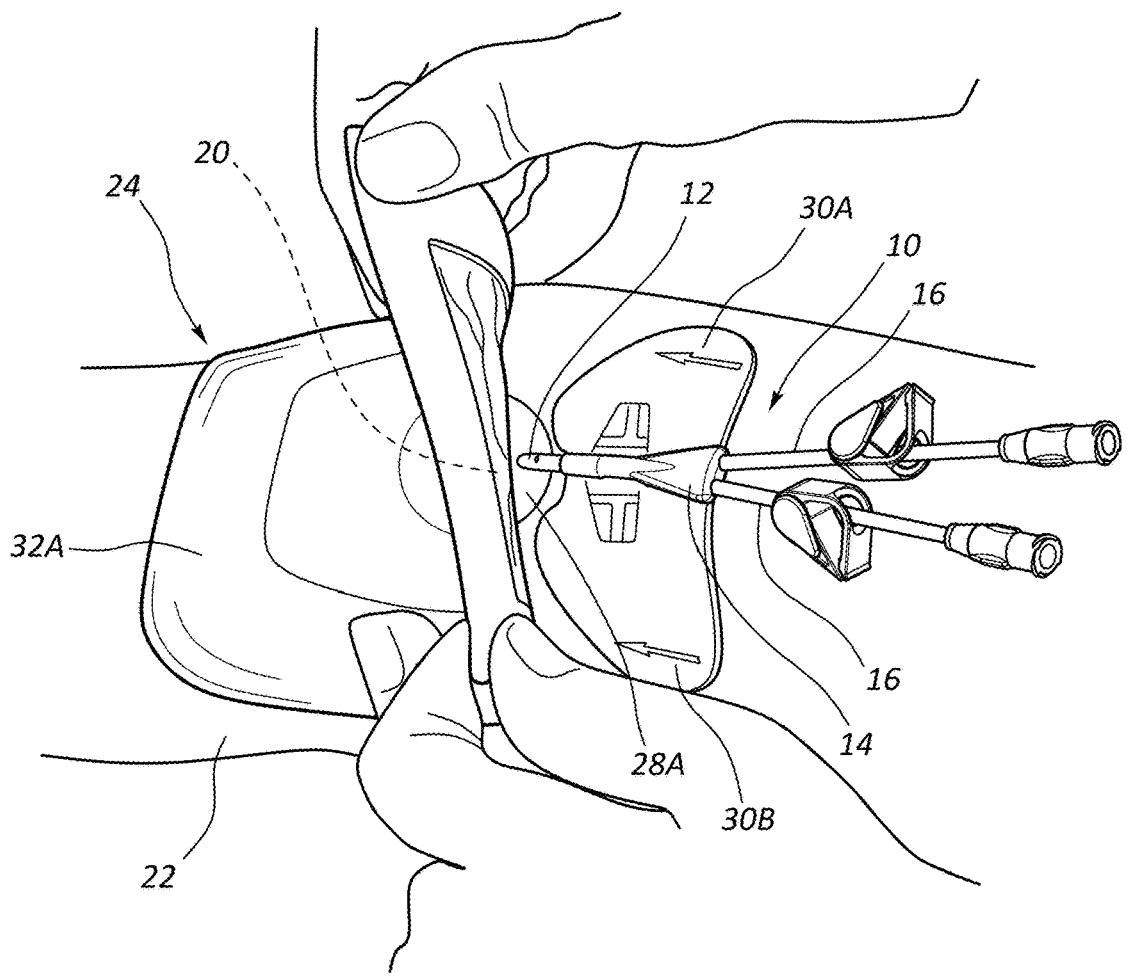
FIG. 1 is a perspective view of a catheter inserted into a body of a patient, exhibiting one example environment where one embodiment can be practiced.

Reference is first made to FIG. 1, which depicts a catheter 10 including a catheter tube 12 inserted transcutaneously through a skin 22 of a patient 24 via an insertion site 20. Though the catheter 10 shown here is a PICC, various other catheters and medical devices can benefit from the principles and features described below. Examples of other catheters and elongate tubular devices include dialysis catheters, Foley and urinary catheters, feeding tubes, balloon catheters, PIVs, etc. Vascular and other types of access ports are further examples of medical devices that may be employed. Also, though shown here inserted into the arm of the patient 24, the catheter 10 or other medical device can be disposed in other areas of the body of the patient, not only transcutaneously, but topically or subcutaneously as well. In another embodiment, the medical device is not connected to or in contact with the patient's body. Thus, these and other modifications are therefore contemplated.

FIG. 1 further shows that the catheter 10 includes a bifurcation hub 14 and a plurality of extension legs 16 that operably connect, via the hub, to a corresponding number of lumens defined by the catheter tube 12. An antimicrobial/hemostatic patch 28A, such as a GUARDIVA® dressing from Bard Access Systems, Inc. of Salt Lake City, UT, is disposed about the catheter tube 12 at the insertion site 20, and a catheter securement device 30A, such as a STAT-LOCK® securement device available from Bard Access Systems, Inc., is removably attached to the patient skin 22 so as to removably attach to and secure the hub 14 of the catheter. An adhesive dressing 32A, such as a TEGADERM® dressing available from 3M, St. Paul, Minnesota, is adhesively and removably positioned so as to cover the external portion of the catheter 10, the patch 28A, and the securement device 30A and isolate the insertion site 20 and protect it from contamination. The patch 28A, the securement device 30A, and the adhesive dressing 32A are collectively referred to herein as a "dressing assembly" or "dressing," though it is appreciated that more or fewer components can be included in the assembly.

As shown in FIG. 1, it is periodically necessary to change the current/existing dressing assembly of the indwelling catheter 10 and replace it with a new dressing assembly. As such, FIG. 1 shows the patch 28A, the securement device 30A, and the adhesive dressing 32A as old components needing to be changed. Indeed, FIG. 1 shows the old adhesive dressing 32A being removed from the patient skin 22 by a clinician.

Figure 2:
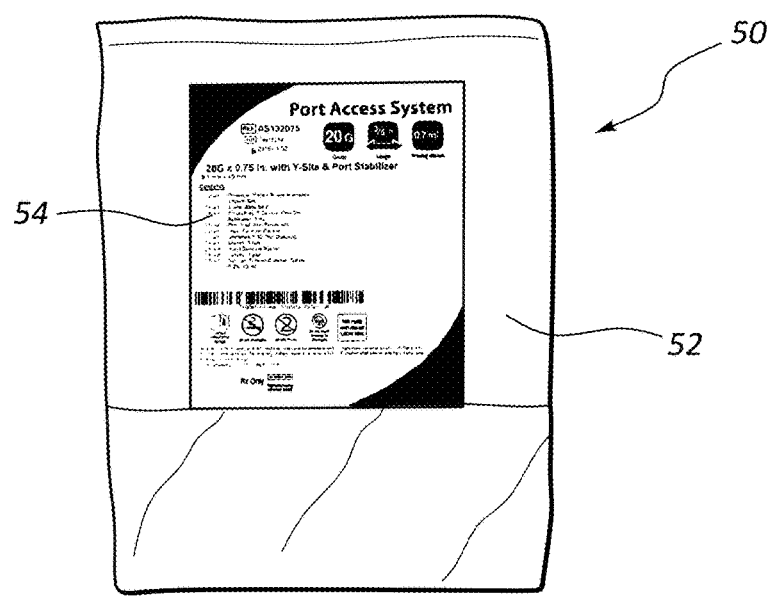
FIG. 2 is a top view of a medical device kit according to one embodiment.

FIG. 2 shows a medical device kit ("kit") 50 according to one embodiment, which can be used in a procedure to replace the old dressing assembly with a new dressing assembly for an indwelling catheter, such as the catheter 10 shown in FIG. 1. The kit 50 of FIG. 2 is thus also referred to in the present embodiment as a dressing change kit and includes various components needed to perform a dressing assembly change procedure, though it is appreciated that the kit can be configured for one or more of a variety of procedures involving a medical device. The discussion to follow is therefore illustrative and is not to be considered as limiting. As shown, the kit 50 here includes a translucent pouch 52 in which the components of the kit are enclosed, and a label 54 to identify the kit. The pouch may be configured in other ways in addition to that shown and described herein.

Figure 3A:
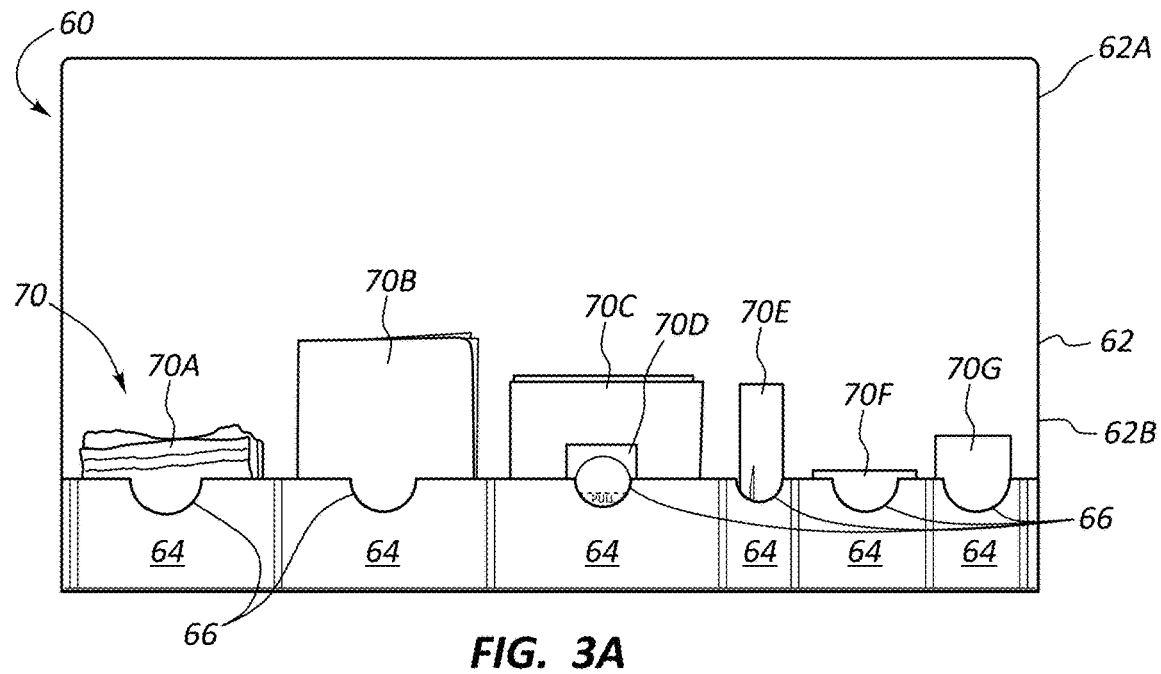
FIGS. 3A-3G are various views of a wrap for inclusion in the medical device kit of FIG. 2.

FIG. 3A depicts various details of a wrap assembly, namely, a removal wrap assembly 60, configured according to one embodiment. The wrap assemblies to be described herein are employed in one embodiment to serve as a platform and a sterile surface for supporting the components of the kit, as will be described below. In the present embodiment, the removal wrap assembly 60 is included in the kit 50 and is configured herein to serve as a platform for components typically used in the changing of the dressing assembly for the catheter 10. Note that the wrap assemblies to be described herein can be configured to be used in a variety of ways and in various kits for use with many different medical devices.

In greater detail, the removal wrap assembly 60 includes a substantially flat, flexible and foldable wrap body 62, including a spunbond-meltblown-spunbond ("SMS") non-woven fabric or other suitable material/fabric. In the present embodiment, the material of the wrap body 62 includes a density of about 60 grams per square meter ("GSM"), though other densities are possible. The wrap body 62 includes a front surface, shown in FIG. 3A, and an opposite back surface. The wrap body 62 is further divided into a top portion 62A and a bottom portion 62B, as shown in FIG. 3A. In one embodiment, the wrap body described herein is about 22" by 22" square, though a variety of other sizes are also possible according to need and intended use, etc.

Figure 3B:
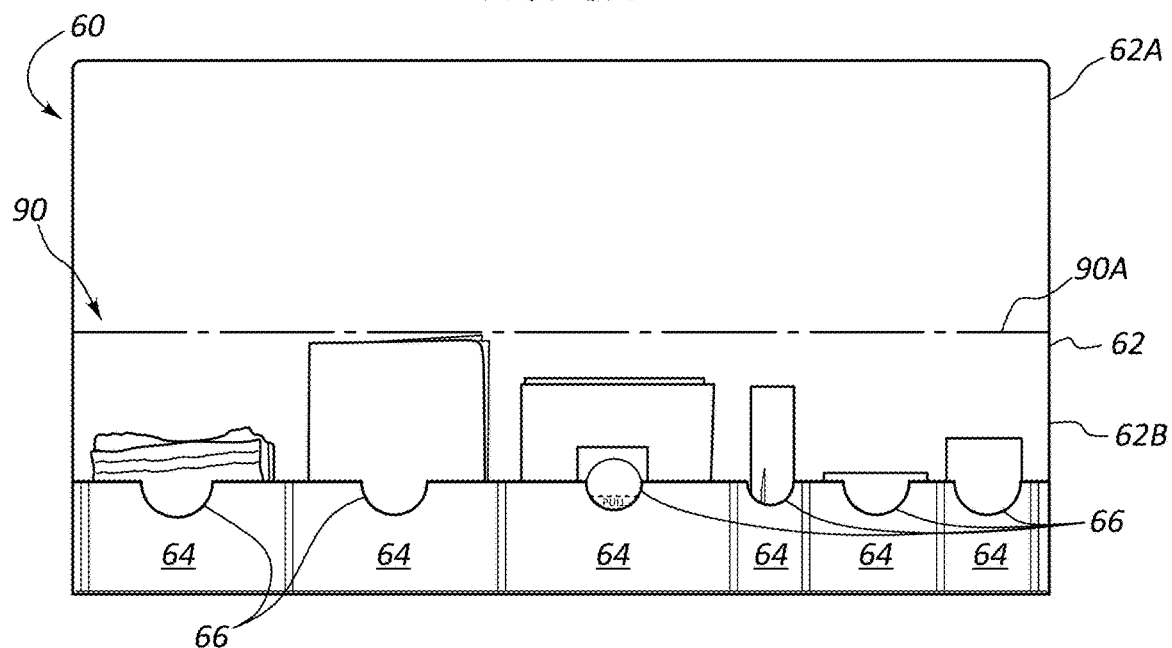

The front surface of the wrap body 62 includes a plurality of pockets 64 aligned along the bottom edge of the bottom portion 62B, as seen in FIGS. 3A and 3B. The material defining the pockets 64 includes SMS nonwoven fabric, like other portions of the wrap body 62, or other suitable material/fabric. In the present embodiment, the material defining the pockets 64 is a single piece of wrap material and is ultrasonically welded to the front surface of the wrap body 62 so as to define the bottom and sides of each of the separate pockets 64 with the top of each pocket being open. In another embodiment an adhesive, such as hot glue, or other suitable fixation mode can be employed to secure the pocket material to the wrap body 62. In yet another embodiment, the pockets described herein can be formed by folding an edge portion of the wrap body over on itself then securing it to the underlying portion of the wrap body.

Each of the pockets 64 is sized to receive therein a corresponding one or more of a plurality of removal components 70 that are to be used during a removal procedure to remove the old dressing assembly from the catheter 10. In the present embodiment, the removal components 70 include, from left to right as shown in FIGS. 3A and 3B, a pair of masks 70A, a drape 70B, a hand sanitizer 70D glued via glue dot (or attached via a sticker or other adhesive mode) to a pair of gloves 70C, a tape measure 70E, three alcohol prep pads 70F, and tape strips 70G. In the present embodiment, the removal components 70 are positioned from left to right in the predetermined order that they are to be used by the clinician when performing the removal procedure to remove the old dressing assembly from the catheter 10. The components could vary in number, type, position, etc., in other embodiments, however. Similarly, the size, shape, number, and configuration of the pockets themselves can vary from what is shown and described herein. In the present embodiment, the wrap body includes six pockets, though other numbers of pockets can be included.

In the present embodiment, each pocket 64 also includes a notch 66 to facilitate removal of a component from the particular pocket. Note that the front surface of the removal wrap body 62 as shown in FIGS. 3A and 3B provides a clean environment for use the of the removal components 70, which are also in a medically clean state. Indeed, in one embodiment, the kit 50 is subjected to sterilization procedures sufficient to render the front surface of the wrap body 62 a sterile field for each of the components 70, which are also sterilized. The view of the removal wrap assembly 60 in FIGS. 3A and 3B shows how the wrap assembly would be typically positioned during a removal procedure to remove an old dressing assembly. In another embodiment, the front surface of the wrap body 62 is configured as a clean surface instead of a sterile surface, e.g., the front surface is suitable for a procedure where only a clean field is required, as opposed to a sterile field. In other embodiments, the front or other surface of the wrap body can be configured as other field types, including aseptic, in one embodiment.

Figure 3C:
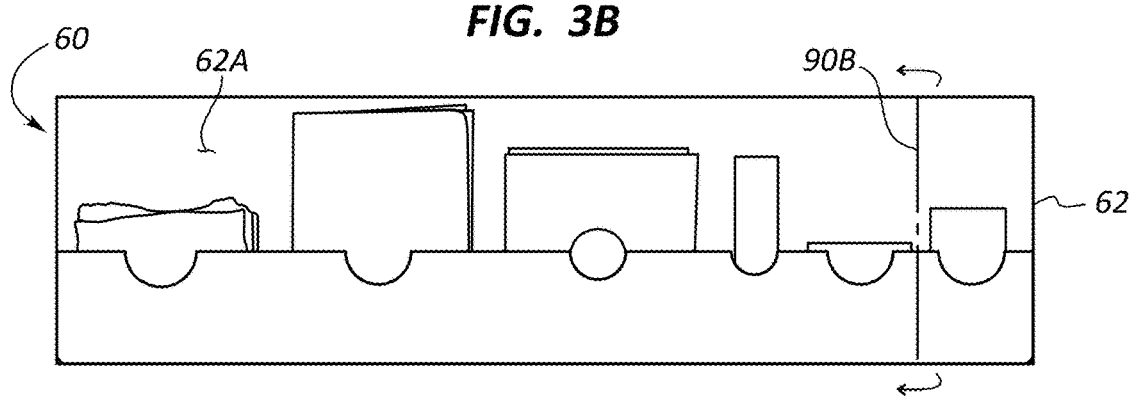
Figure 3D:
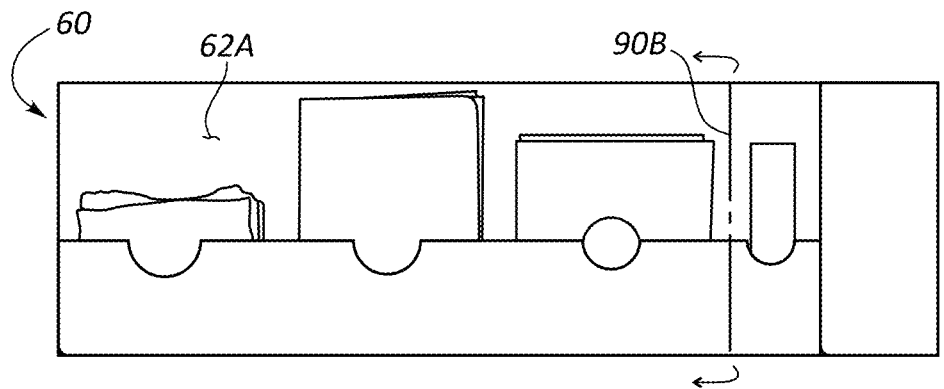
Figure 3E:
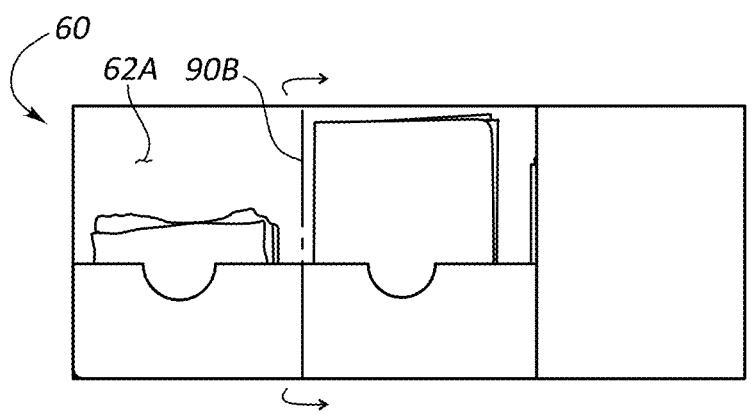

FIGS. 3B-3G depict various stages of the folding of the wrap assembly 60 along various fold lines 90 so as to be packaged in the pouch 52 of the kit 50 (FIG. 2) during kit manufacture. FIG. 3B shows that an imaginary lateral fold line 90 substantially bisects the wrap body 62 to define the wrap body top portion 62A and a wrap body bottom portion 62B. The wrap body 62 is first folded along a lateral fold line 90A such that the wrap body top portion 62A is folded atop the wrap body bottom portion 62B to cover the removal components 70, as seen in FIG. 3C. Folding of the wrap body 62 in this manner covers and preserves the clean and/or sterile state of the removal components 70.

Figure 3F:
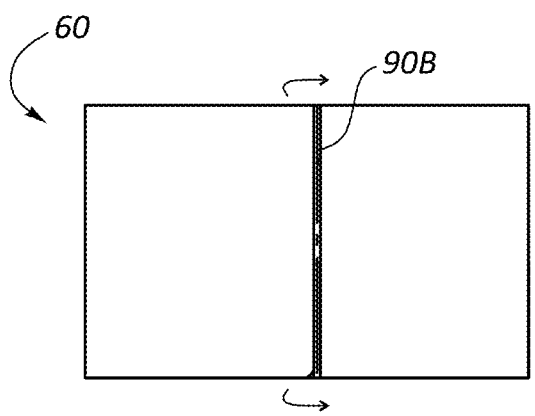
Figure 3G:
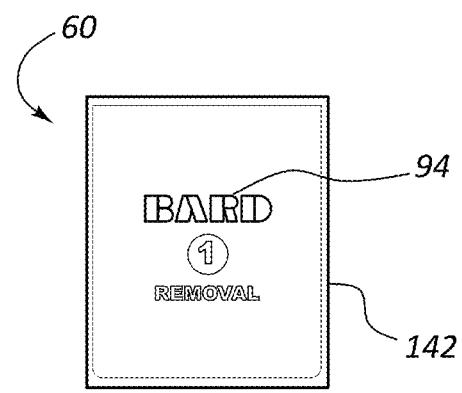

FIGS. 3C-3F shows that imaginary vertical fold lines 90B are successively used to laterally fold the wrap body 62 inward first from the right end (FIG. 3C, the vertical fold line being between the covered pockets 64 containing the alcohol prep pads 70F and the tape strips 70G), inward again from the right end (FIG. 3D, the vertical fold line being between the covered pockets containing the gloves 70C and the measuring tape 70E), inward from the left end (FIG. 3E, the vertical fold line being between the covered pockets containing the masks 70A and the drape 70B), and inward again from the left end (FIG. 3F, the vertical fold line being between the covered pockets containing the drape 70B and the gloves 70C). Folding in this manner produces a removal pack 142 including the folded removal wrap assembly 60 shown in FIG. 3G. FIG. 3G further shows that, in one embodiment, insignia 94 can be included on a selected surface(s) of the wrap body 62 as here, where the insignia indicates a brand name and an identifier of the wrap. Note that a variety of insignia conveying various types of information can be included in one or more areas/surfaces of the wrap body, including documentation, instructions, trademarks, etc. Note also that in this and other embodiments, a variety of different folding configurations can be employed for the wraps of the kits described herein. Unfolding of the removal wrap assembly 60 when use of the kit 50 is commenced occurs in reverse fashion to what is shown and described above. In another embodiment, it is appreciated that the wrap body can be rolled up instead of folding or otherwise reduced in size suitable for packaging in a pouch or other container.

Figure 4A:
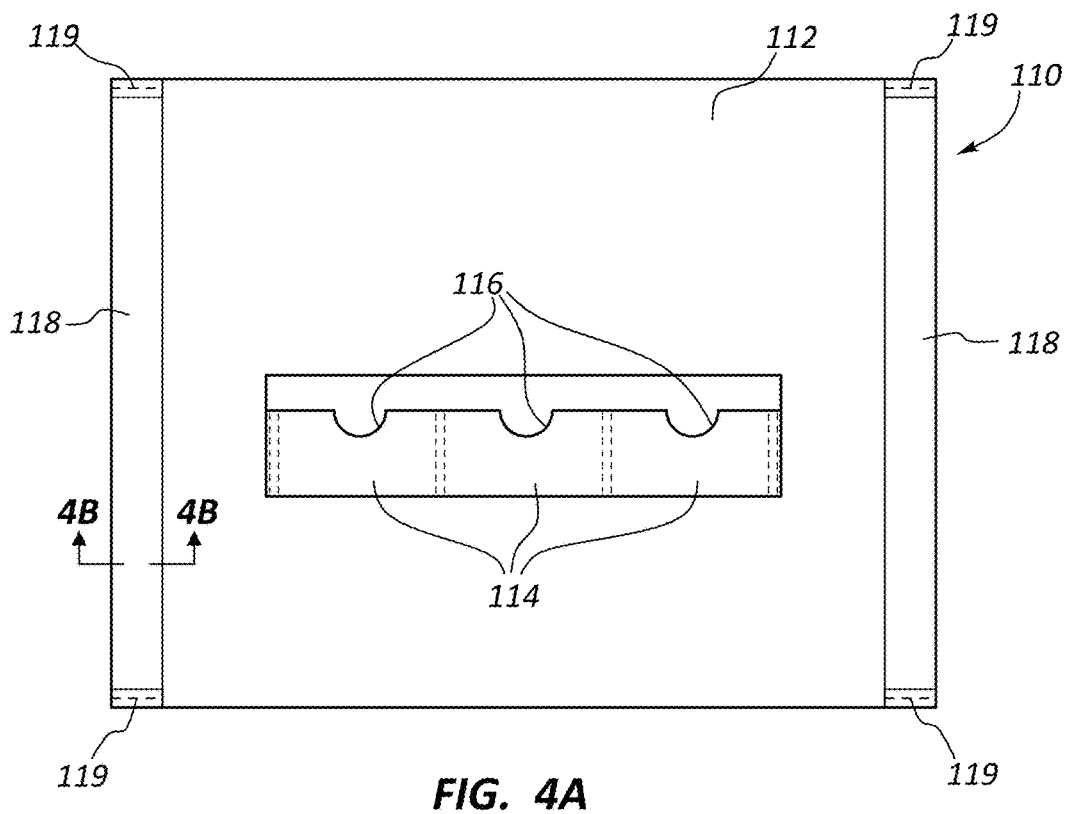
FIGS. 4A and 4B depict various views of a wrap for inclusion in the medical device kit of FIG. 2.

FIG. 4A depicts various details of a wrap body as part of an application wrap assembly 110, configured according to one embodiment. In the present embodiment, the application wrap assembly 110 is included in the kit 50, like the removal wrap assembly 60 described above, and serves as a platform for including various components that are used in placing a new dressing assembly over the catheter 10.

In greater detail, the application wrap assembly 110 includes a substantially flat, flexible and foldable wrap body 112, including a SMS nonwoven fabric of about 60 GSM (though other materials may be acceptably used). The wrap body 112 includes a front surface, shown in FIG. 4A, and an opposite back surface, as shown in FIG. 5.

Figure 6:
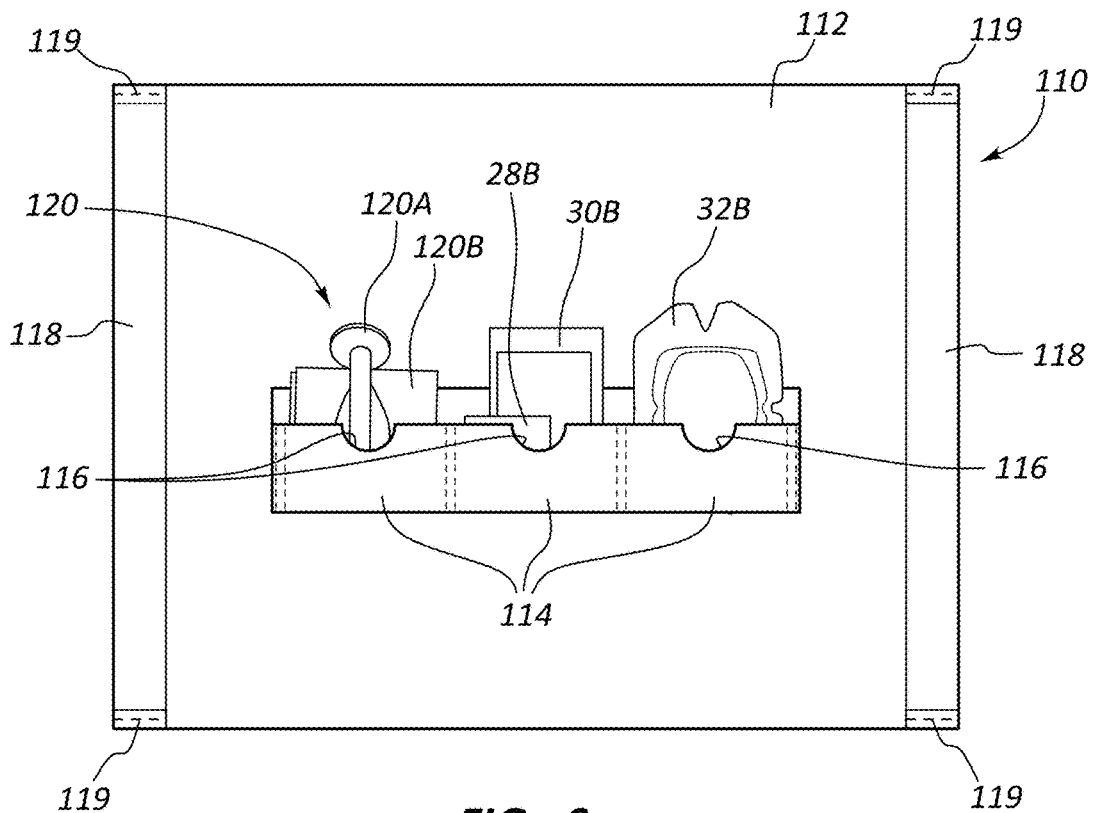
FIG. 6 is a top view of a wrap for inclusion in the medical device kit of FIG. 2.

The front surface of the wrap body 112 includes a plurality of pockets 114 located in a component placement area in a middle portion of the front surface of the wrap body 112. The pockets 114 are aligned along a central portion of the front surface of the wrap body, as seen in FIGS. 4A and 6. The material defining the pockets 114 includes SMS nonwoven fabric or other suitable material/fabric. In one embodiment, the material defining the pockets 114 can include a thermoplastic such as polypropylene, for instance. In the present embodiment, the material defining the pockets 114 is a single piece and is ultrasonically welded (or otherwise suitably attached) to the front surface of the wrap body 112 so as to define the bottom and sides of each of the separate pockets 114 with the top of each pocket being open. The present embodiment includes three pockets 114, though other numbers of pockets are possible. In another embodiment an adhesive, such as hot glue, can be employed to secure the pocket material to the wrap body 112. Note that each pocket 114 also includes a notch 116 to facilitate removal of a component from the particular pocket.

Figure 4B:
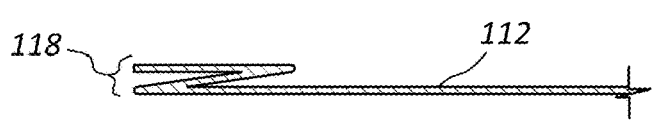
Figure 7:
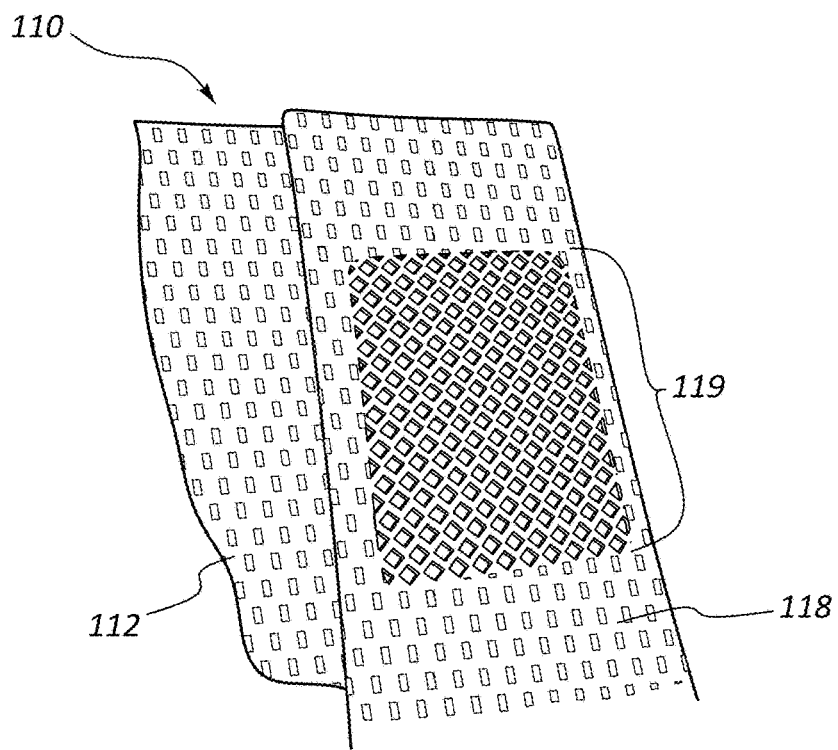
FIG. 7 shows a portion of the wrap of FIG. 6.

The wrap body 112 further includes folded edges on each lateral end of the wrap body to prevent components from sliding off the edge of the wrap body. The folded edges 118 are compound folds, formed by folding a portion of each lateral edge inward, then outward (to form an S-shaped cross-sectional configuration) before tacking the folded edges down, such as via ultrasonic welding. FIG. 4A shows a plurality of weld points 119 where the ultrasonic welding occurs. FIG. 4B shows a cross sectional view of the folded edge 118 according to the present embodiment. FIG. 7 shows a close-up of one of the weld points 119, in one embodiment. The folded edges 118 are further configured to enable a clinician to grasp the edges of the wrap body without touching the front surface of the wrap body, which would otherwise potentially compromise the sterility of the front surface sterile field, as discussed below. In one embodiment, the folded edges can be included on edge of the wrap body.

Figure 5:
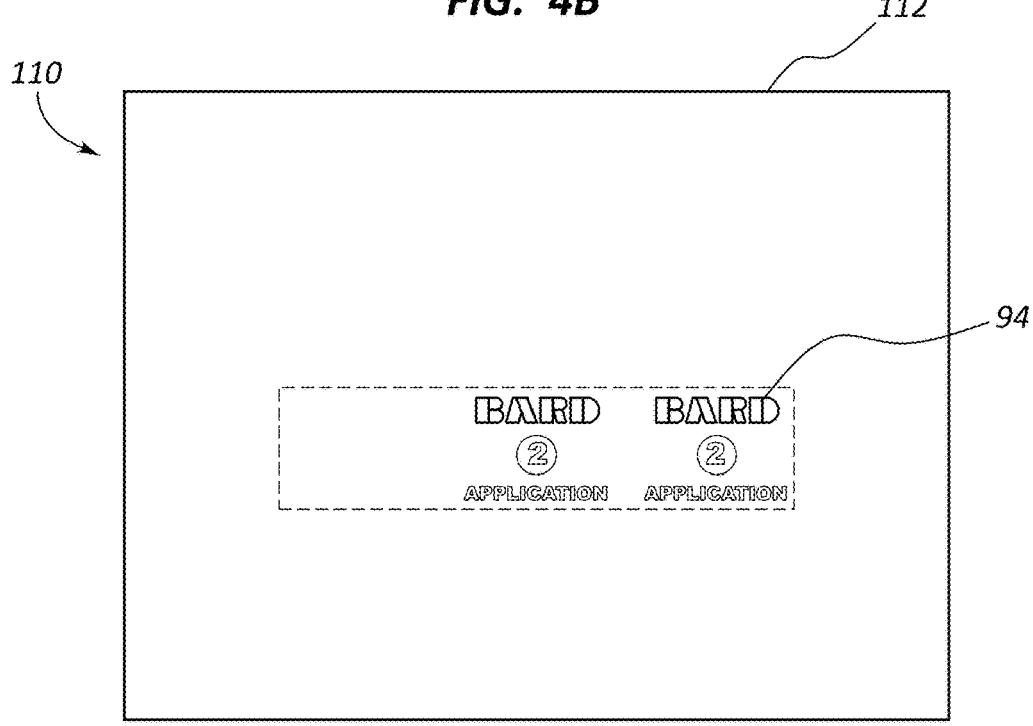
FIG. 5 is a bottom view of the wrap of FIG. 4A.

FIG. 5 shows another example of the insignia 94 as placed on the back surface of the wrap body 112 in the present embodiment, indicating a brand name and an identifier of the wrap. Of course, the position and content/purpose of the insignia can vary from what is shown and described herein.

Reference is now made to FIG. 6. Each of the three pockets 114 of the wrap body 112 is sized to receive therein a corresponding one of a plurality of application components 120 that are to be used during an application procedure to apply a new dressing assembly to the catheter 10. In the present embodiment, the application components 120 include, from left to right as shown in FIG. 6: a CHLORAPREP® solution applicator (CareFusion Corp.) 120A and a gauze 120B; an antimicrobial/hemostatic patch 28B (such as a GUARDIVA® dressing) and a securement device 30B (such as a STATLOCK® securement device); and an adhesive dressing 32B (such as a TEGADERM® dressing), wherein the last three components comprise the new dressing assembly. In the present embodiment, the application components 120 are positioned from left to right in the order that they are to be used by the clinician when performing the application procedure to apply a the new dressing assembly over the catheter 10. The components could vary in number, type, position, etc., in other embodiments, however. Similarly, the size, shape, number, and configuration of the pockets themselves can vary from what is shown and described herein.

Note that, in one embodiment, the front surface of the application wrap body 112 as shown in FIG. 6 provides a sterile environment for use the of the application components 120, which are sterilized. The view of the application wrap assembly 110 in FIG. 6 shows how the wrap body 112 would be typically positioned during an application procedure to apply the new dressing assembly. As such, the application wrap body 112 comprises part of a sterile field for applying the new dressing assembly, in one embodiment.

Figure 8A:
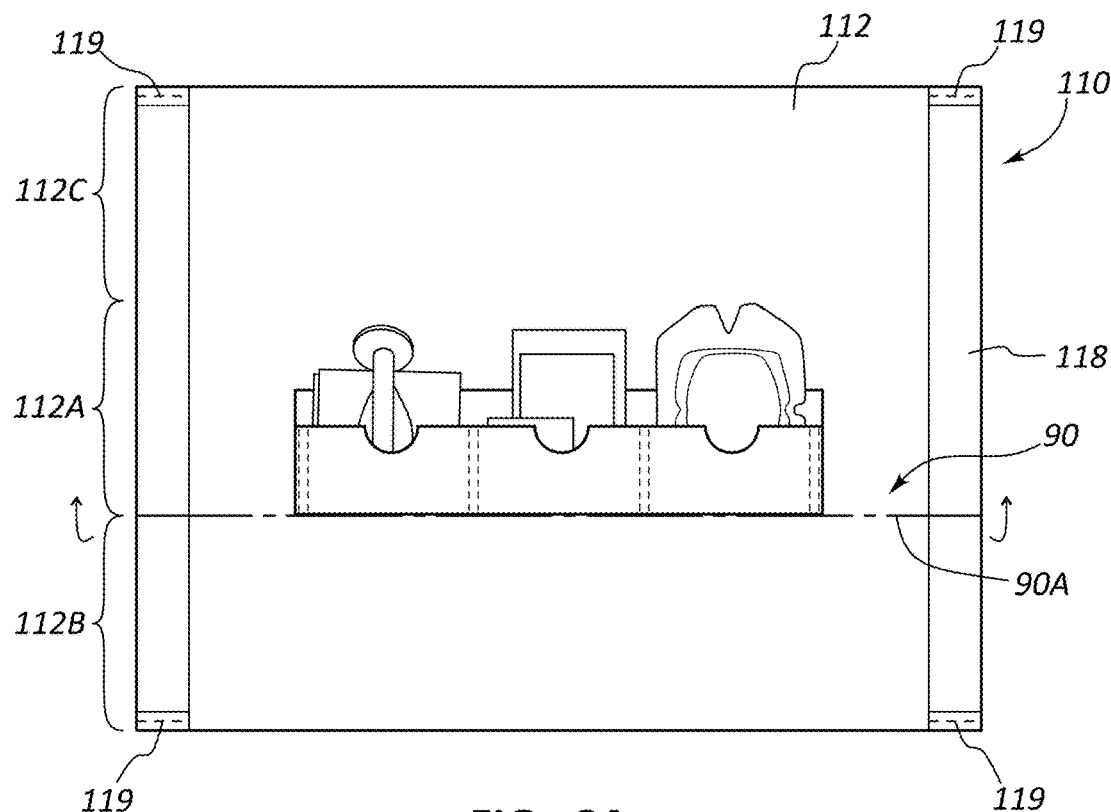
FIGS. 8A-8G are various views of the wrap of FIG. 6.
Figure 8B:
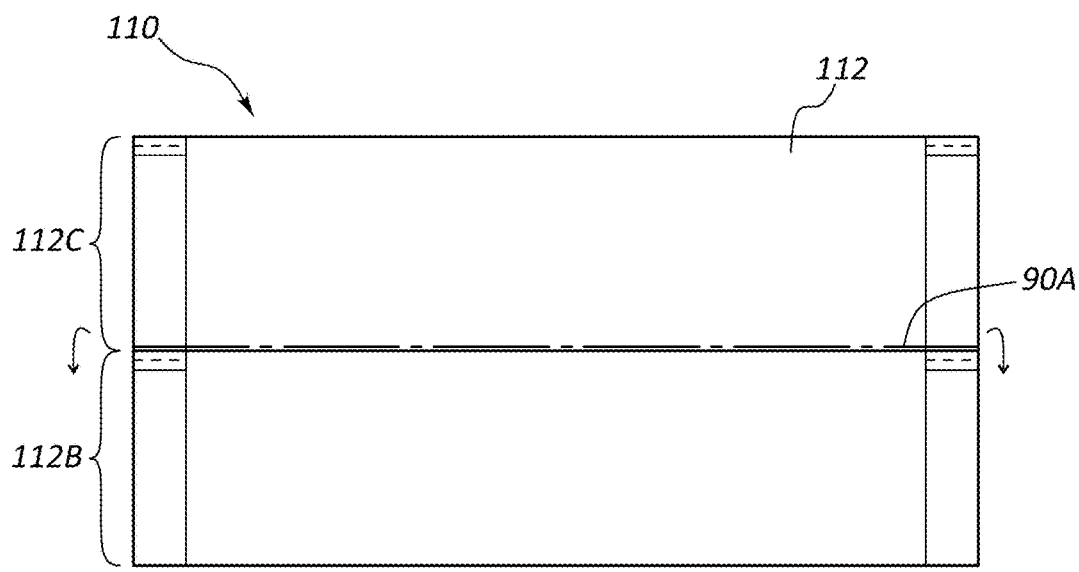
Figure 8C:
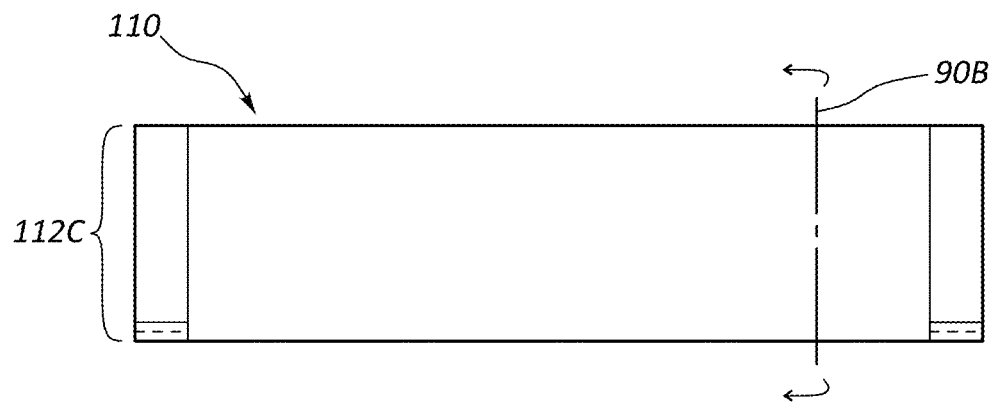

FIGS. 8A-8G depict various stages of the folding of the application wrap assembly 110 along various imaginary fold lines 90 so as to be packaged in the pouch 52 of the kit 50 (FIG. 2), together with the removal wrap assembly 60, during kit manufacture. FIGS. 8A and 8B show that lateral fold lines 90A substantially divide the wrap body 112 to define a wrap body bottom portion 112A, a wrap body intermediate portion 112B, and a wrap body top portion 112C. To fold the wrap body 112, the intermediate portion 112B thereof is first folded along a lateral fold line 90A so as to cover the bottom portion 112A and substantially cover the application components 120 within the pockets 114 that are attached to the bottom portion, as seen in FIG. 8B. The top portion 112C is then folded atop the intermediate portion 112B along a corresponding lateral fold line 90A shown in FIG. 8B to provide the wrap body configuration shown in FIG. 8C. Folding of the wrap body 112 in this manner covers and preserves the sterile state of the application components 120.

Figure 8D:
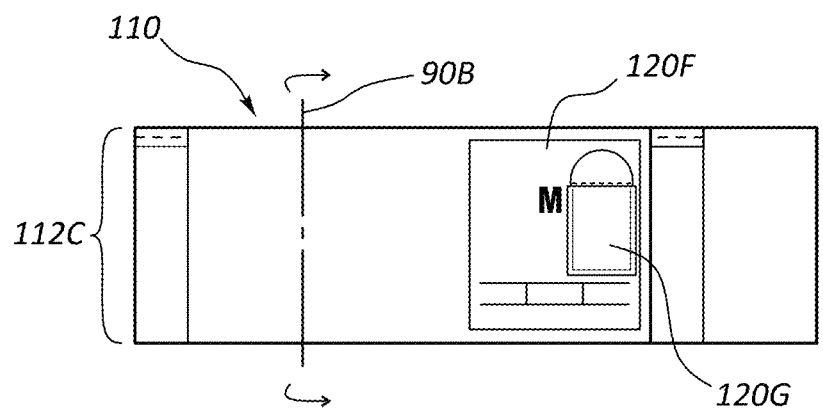
Figure 8E:
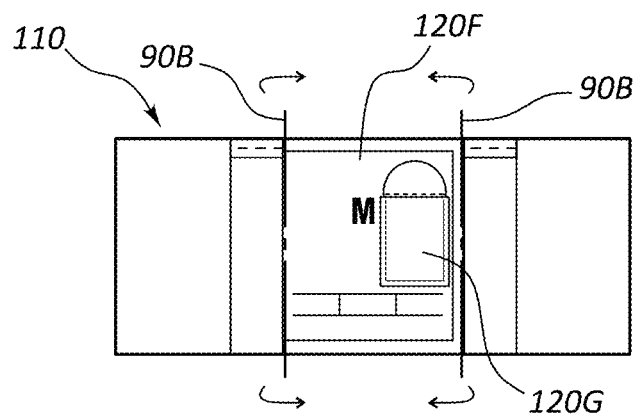
Figure 8F:
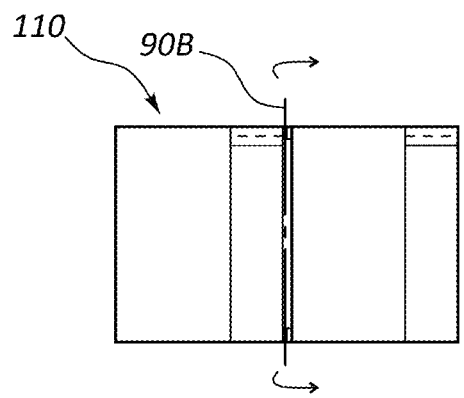
Figure 8G:
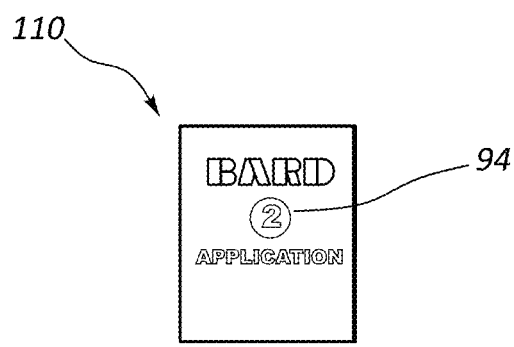

FIGS. 8C-8F show that imaginary vertical fold lines 90B are successively used to laterally fold the wrap body 112 inward first from the right end (FIG. 8C), then inward from the left end (FIG. 8D). A pair of gloves 120F and an adhesively attached (such as via a sticker) hand sanitizer packet 120G are then positioned on a central part of the partially folded wrap body 112, before the wrap body is further folded from both the left and the rights ends thereof (FIG. 8E, 8F). Folding in this manner produces an application pack 144 including the folded application wrap assembly 110, as shown in FIG. 8G, with the insignia 94 facing up. Note that the fold lines discussed herein can be printed or otherwise visually indicated on the wrap body if desired, in one embodiment.

Figure 9A:
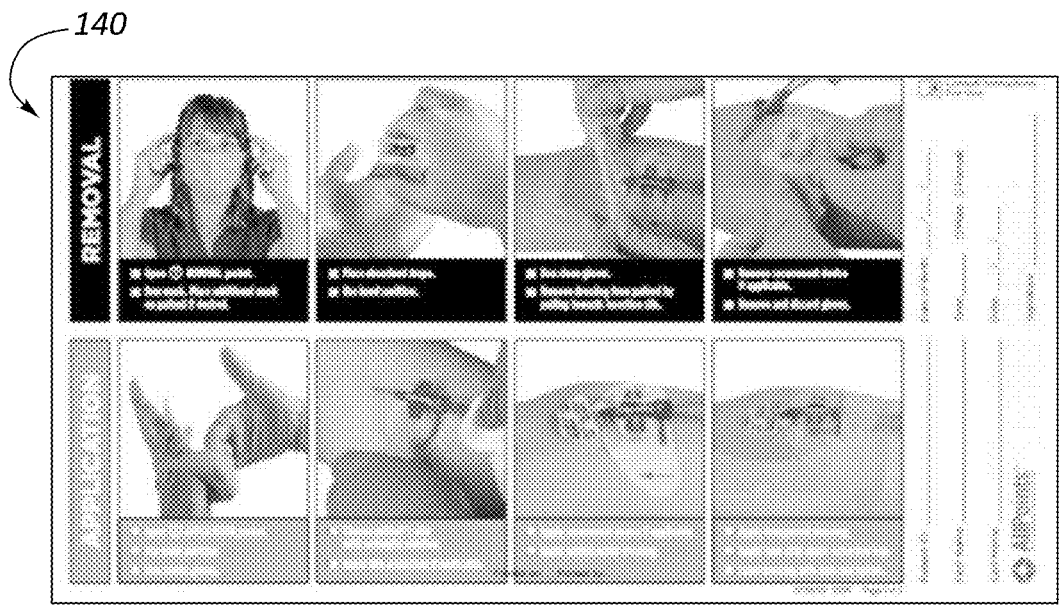
FIGS. 9A and 9B depict various views of documentation for use with the medical device kit of FIG. 2.
Figure 9B:
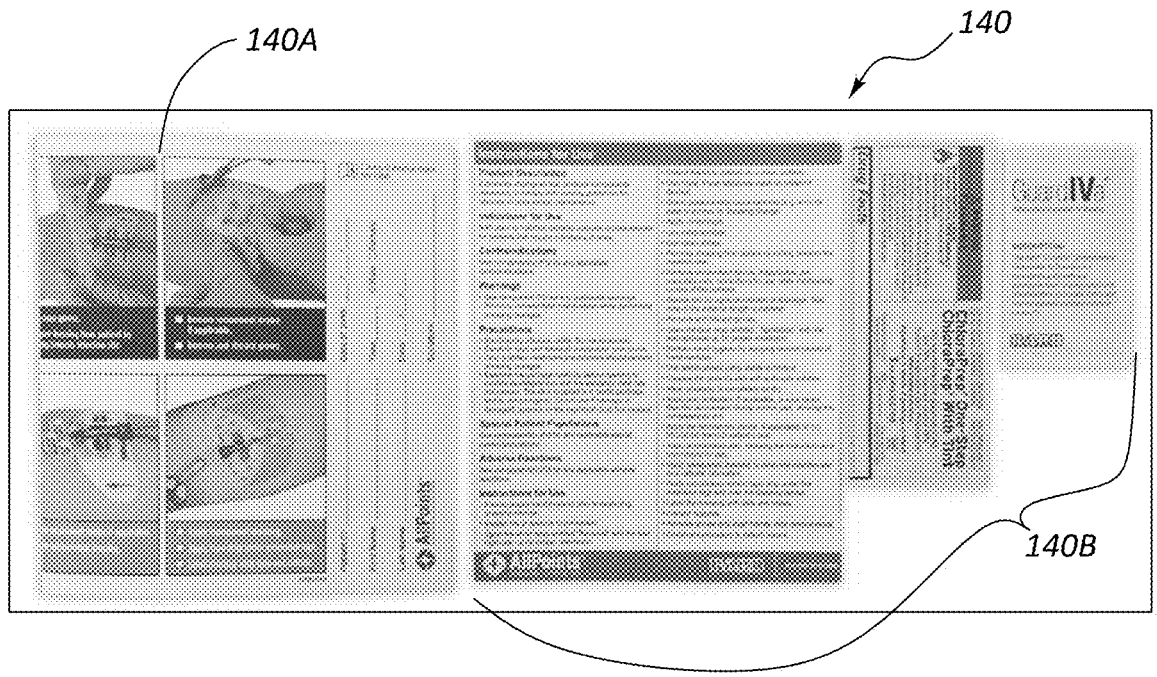

FIGS. 9A and 9B depict documentation 140 to be included in the pouch 52 of the kit 50, including a visual guide 140A and instructions-for-use ("IFUs") 140B for several of the components 170.

Figure 10:
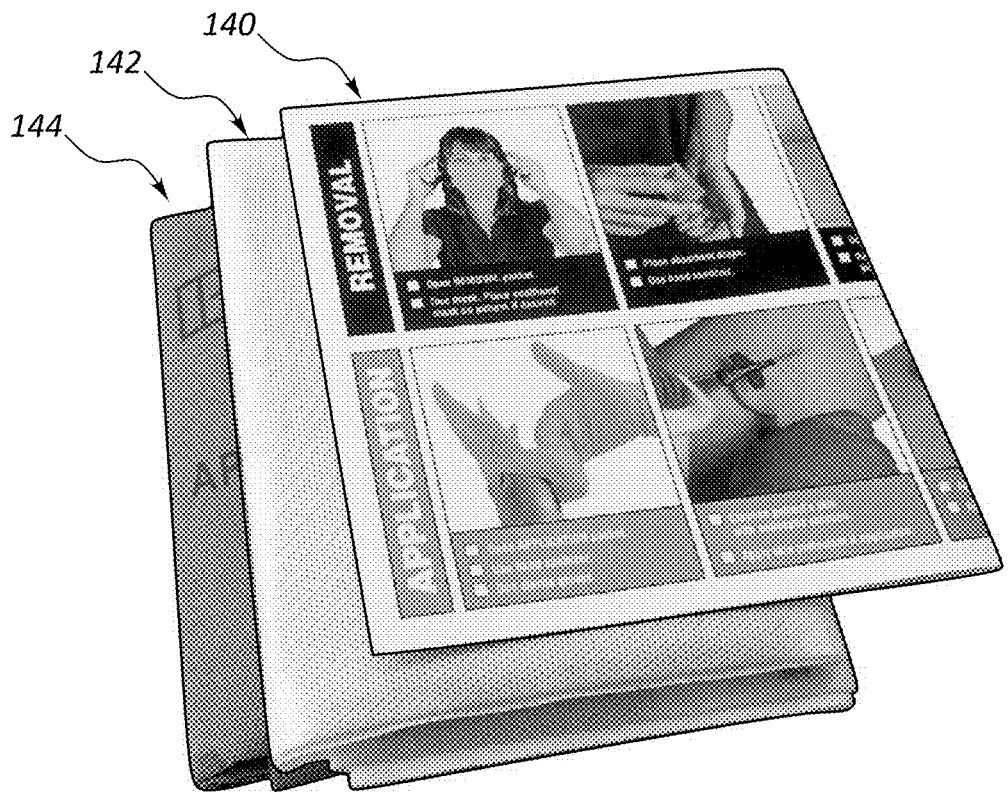
FIG. 10 shows the contents of the medical device kit of FIG. 2 according to one embodiment.
Figure 11A:
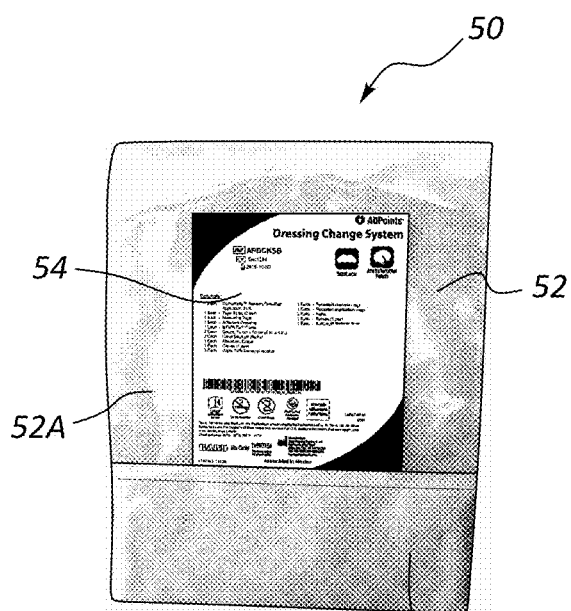
FIGS. 11A and 11B depict various views of the medical device kit of FIG. 2.
Figure 11B:
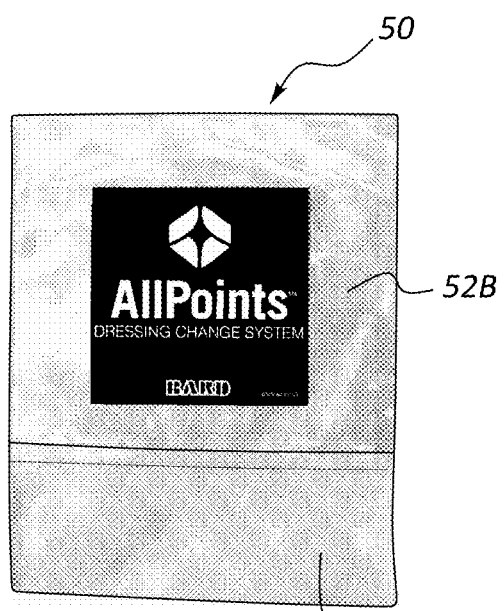

FIG. 10 shows that the documentation 140 is arranged together and stacked atop the folded application pack 144 and the folded removal pack 142 prior to being inserted into the pouch 52 with the label 54 affixed thereto, as seen in FIGS. 11A and 11B. Note that in the present embodiment, the removal wrap assembly 60 is colored blue, while the application wrap assembly 110 is colored white to differentiate the wrap assemblies from one another. Other colors can, of course, be used.

In the present embodiment, the pouch 52 includes a clear bag composed of LDPE, HDPE, and nylon, and further includes a TYVEK® material portion 146 (or other suitable material) that enables gas permeation into the interior of the pouch 52 to sterilize the wrap assemblies and components therewithin during a gas sterilization procedure after sealing of the pouch has been performed. Other suitable sterilization methods can also be performed. The completed kit 50 is shown in FIGS. 11A and 11B after manufacture thereof.

Figure 12:
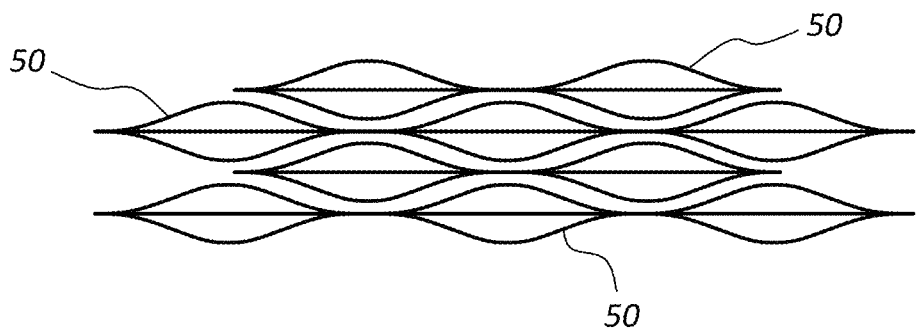
FIG. 12 shows one configuration for stacking a plurality of medical device kits.
Figure 13:
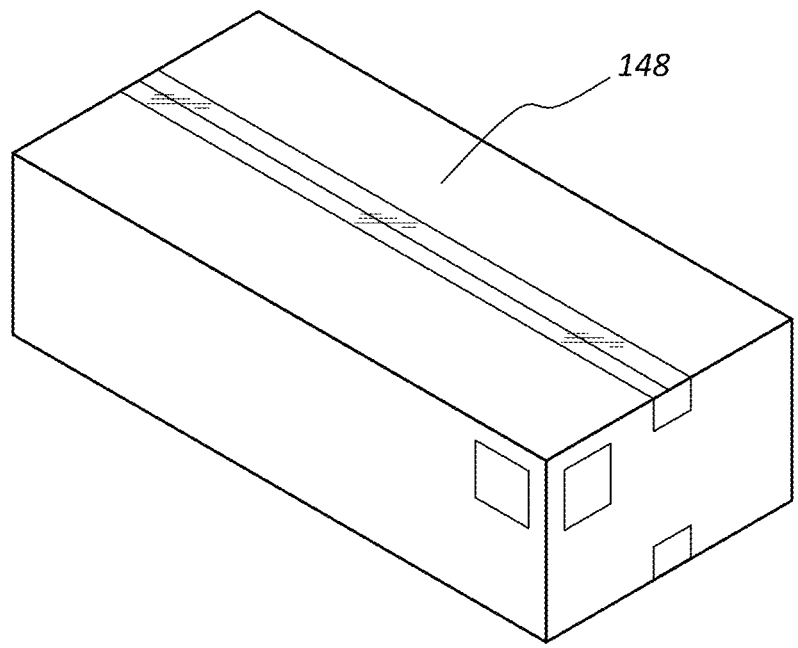
FIG. 13 shows a box loaded with stacked medical device kits according to one embodiment.

FIG. 12 shows one example configuration for stacking the completed kits 50 for placement in a box, such as the box 148 shown in FIG. 13. Other storage and packing configurations are, of course, contemplated.

Figure 14:
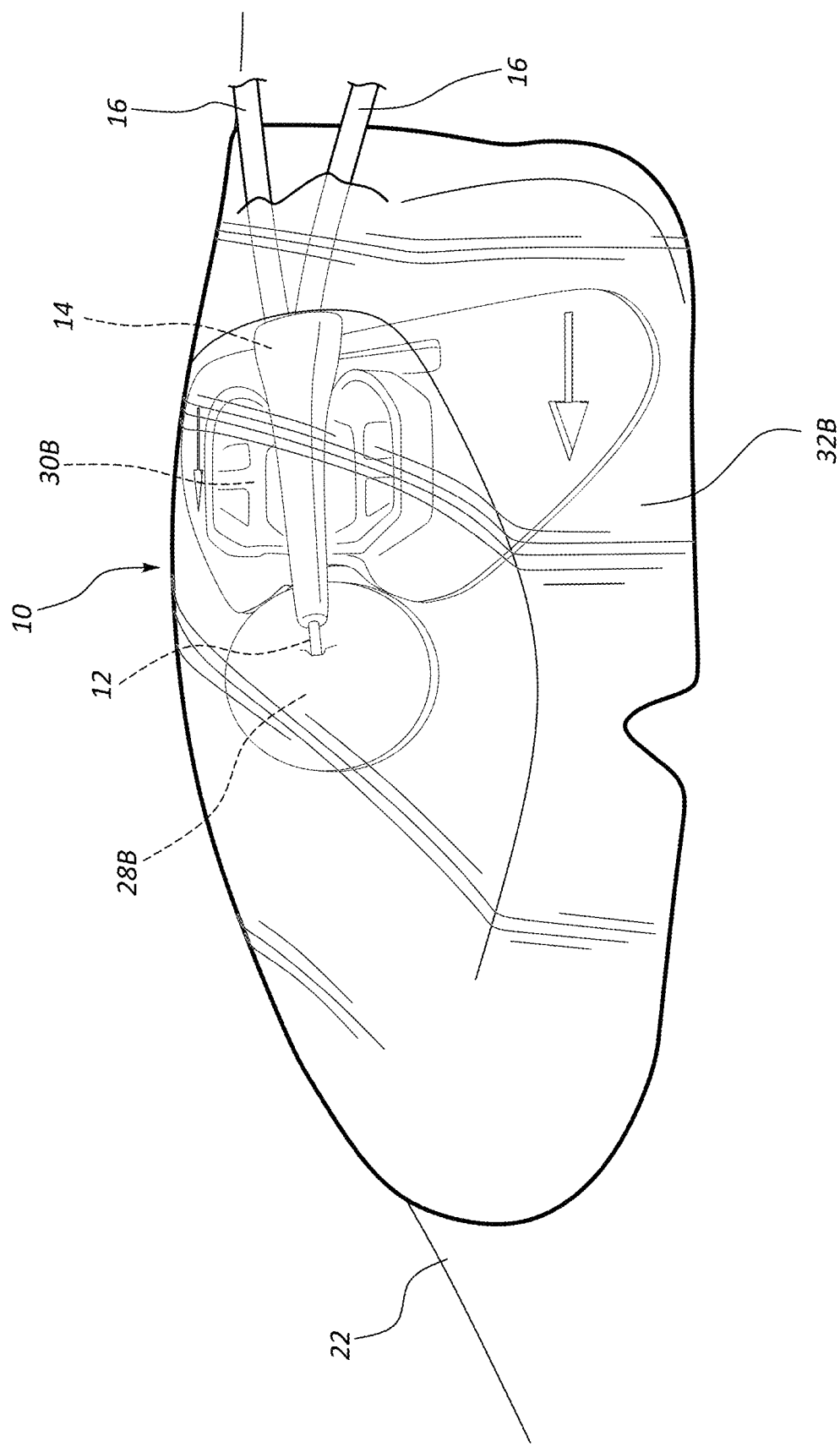
FIG. 14 is a perspective view of a catheter inserted into a body of a patient after use of a medical device kit, according to one embodiment.

FIG. 14 shows the new dressing assembly (comprising in part components included in the application wrap assembly 110 of the application packet 144 of the kit 50) in position after placement over the catheter 10, including the antimicrobial/hemostatic patch 28B, the securement device 30B, and the adhesive dressing 32B. As mentioned, various different kits including or for use with a variety of medical devices can include the wrap assemblies and other component as described above and further below.

Figure 15A:
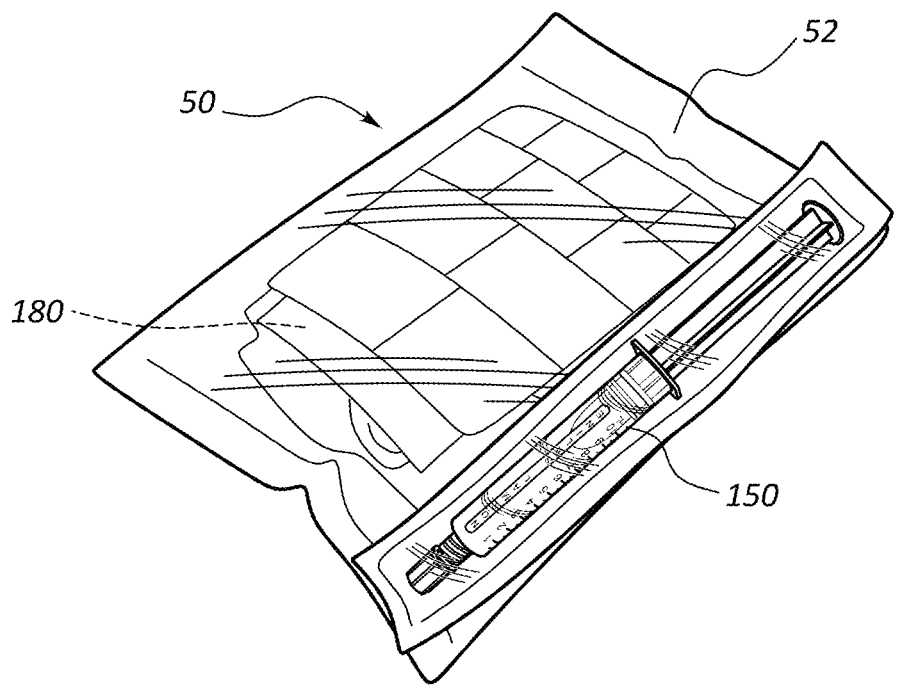
FIGS. 15A and 15B show various views of a medical device kit according to one embodiment.
Figure 15B:
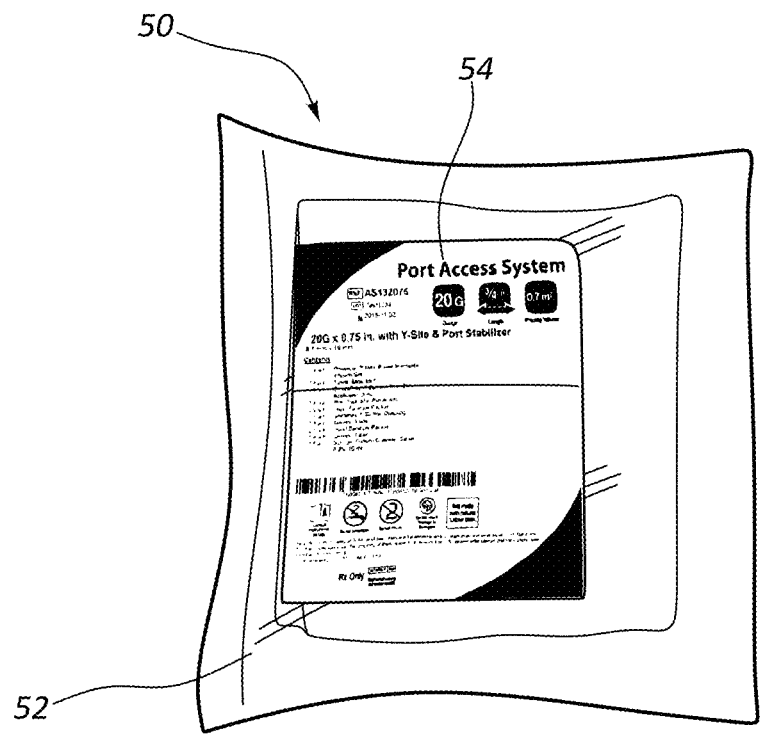

FIGS. 15A and 15B depict various details of the kit 50 according to another embodiment. As shown, the kit 50 is packaged in the translucent pouch 52 through which the documentation 140 can be viewed. FIG. 15B shows that a packaged saline syringe 150 is removably attached to the kit pouch 52, and the label 54 is affixed to the pouch as well. The kit 50 shown here is a port access kit for use by a clinician to establish fluid/needle access to a subcutaneously implanted vascular access port via an infusion needle. Again, the kit can be configured for a variety of uses in relation to medical devices.

Figure 16A:
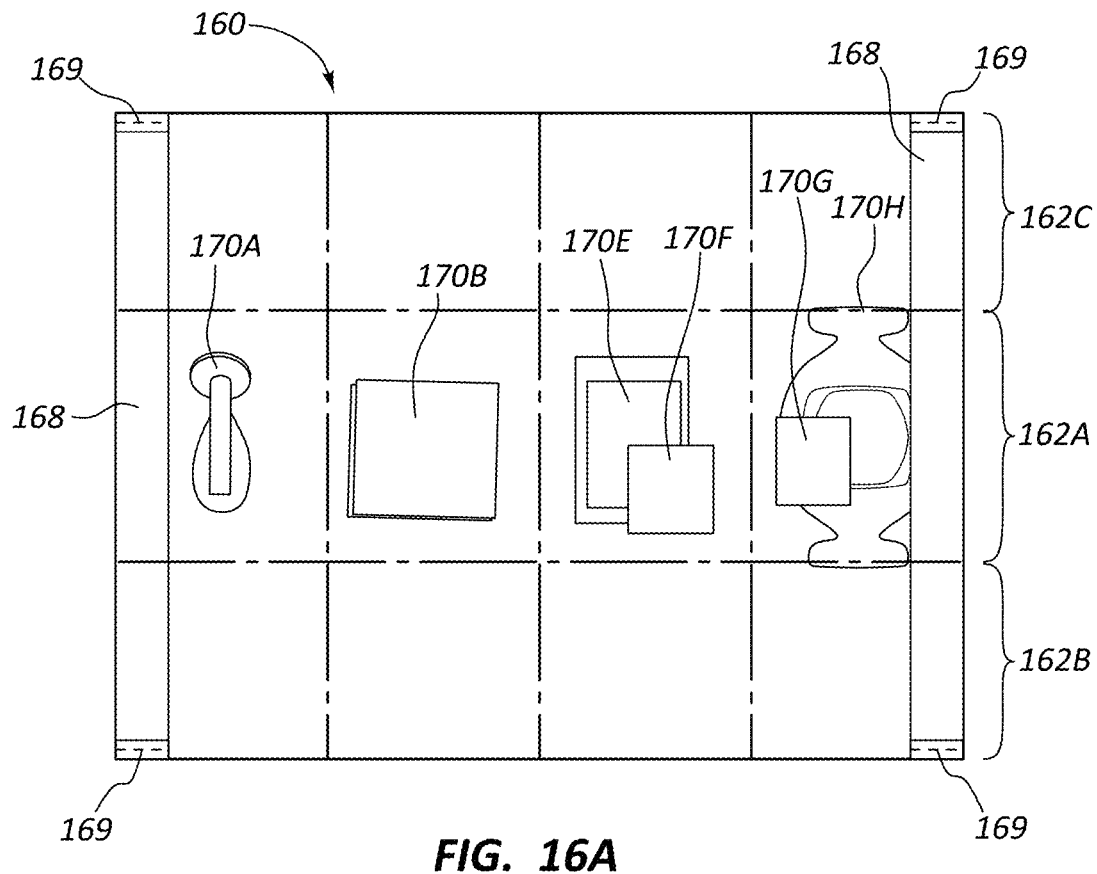
FIGS. 16A-16F are various views of a wrap for inclusion in the medical device kit of FIGS. 15A and 15B.

FIG. 16A depicts various details of a wrap assembly 160, configured according to one embodiment. In the present embodiment, the wrap assembly 160 is included in the kit 50 of FIGS. 15A and 15B and serves as a platform for including various components that are used in accessing an implanted access port with an infusion needle. In greater detail, the wrap assembly 160 includes a substantially flat, flexible and foldable wrap body 162, including a SMS nonwoven fabric of about 60 GSM in the present embodiment. The wrap body 162 includes a front surface, shown in FIG. 16A, and an opposite back surface. The wrap assembly 160 further includes folded edges 168 on each lateral end of the wrap body 162, folded as compound folds in a cross-sectional S-shaped configuration similar to the folded edges 118 of the wrap embodiment discussed in connection with FIG. 6, to prevent components from sliding off the lateral edges of the wrap body. As before, the folded edges 168 are secured by an appropriate fixation, such as via ultrasonic welding.

As shown in FIG. 16A, a plurality of access components 170 that are to be used during a procedure to introduce an infusion needle into an implanted access port are shown disposed at a component placement area atop the front surface of the wrap body 162. In the present embodiment, the access components 170 include, from left to right as shown in FIG. 16A: a CHLORAPREP® solution applicator (CareFusion Corp.) 170A and a drape 170B; an antimicrobial/hemostatic patch (such as a GUARDIVA® dressing) 170F and an infusion needle 170E, such as a POWERLOC® safety infusion set, POWERLOC® MAX safety infusion set, or SAFESTEP® Huber needle set sold by Bard Access Systems, Inc.); and a skin prep pad 170G and an adhesive dressing 170H, such as a SENTRINEX™ 3D port dressing available from Bard Access Systems, Inc. In the present embodiment, the access components 170 are positioned from left to right in the order that they are to be used by the clinician when performing the procedure to access the implanted access port with the infusion needle. As before, the components could vary in number, type, position, etc., in other embodiments.

Note that, in one embodiment, the front surface of the wrap body 162 as shown in FIG. 16A provides a sterile environment for use the of the access components 170, which are sterilized. The view of the wrap assembly 160 in FIG. 16A shows how the wrap would be typically positioned during an access procedure to percutaneously insert the infusion needle into the implanted access port. As such, the wrap assembly 160 comprises part of a sterile field for accessing the implanted access port, in one embodiment. The wrap body 162 can be placed, for instance, on a bedside stand, a table, a bed, or atop the patient.

Figure 16B:
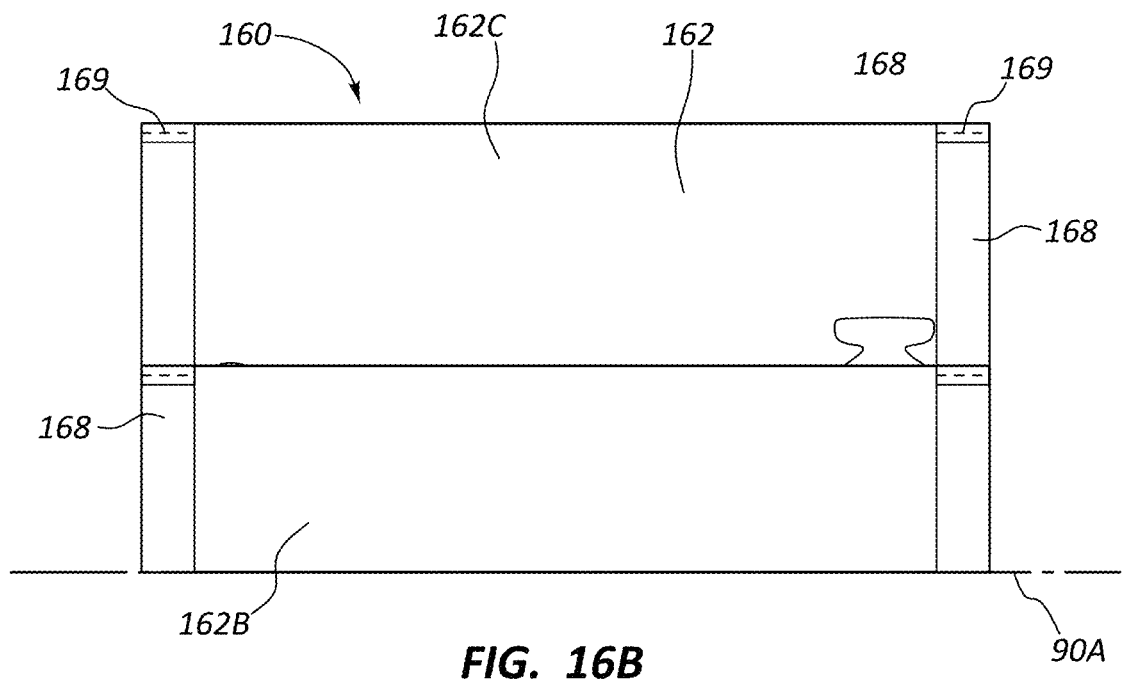
Figure 16C:
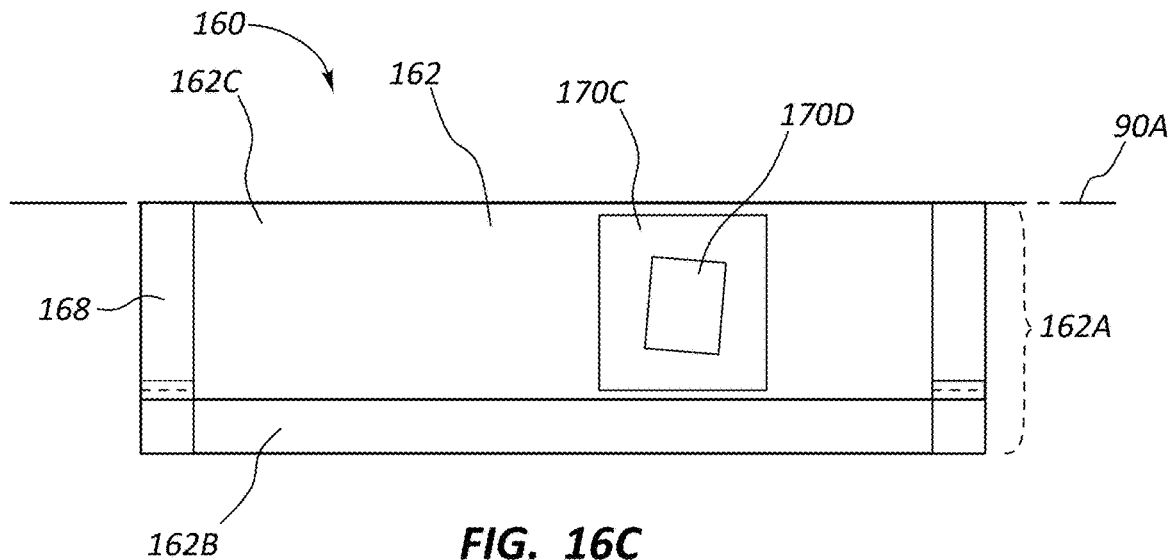

FIGS. 16A-16E depict various stages of the folding of the wrap assembly 160 along various imaginary fold lines 90 so as to be packaged in the pouch 52 of the kit 50 (FIG. 15A) during kit manufacture. FIG. 16A shows that the wrap body 162 includes a wrap body bottom portion 162A, a wrap body intermediate portion 162B, and a wrap body top portion 162C. To fold the wrap body 162, the intermediate portion 162B thereof is first folded along a lateral fold line 90A so as to cover the bottom portion 162A and substantially cover the access components 170 disposed on the component placement area of the bottom portion, as seen in FIG. 16B. The top portion 162C of the wrap body 162 is then folded atop the intermediate portion 162B along a corresponding lateral fold line 90A shown in FIG. 16C to produce the wrap body configuration shown in FIG. 16C. Folding of the wrap body 162 in this manner covers and preserves the sterile state of the access components 170. Note that additional components 170 are placed on the wrap body 162 at this stage: a pair of gloves 170C and an adhesively attached sanitizer packet 170D. In another embodiment these components can be placed with the other components 170 shown in FIG. 16A.

Figure 16D:
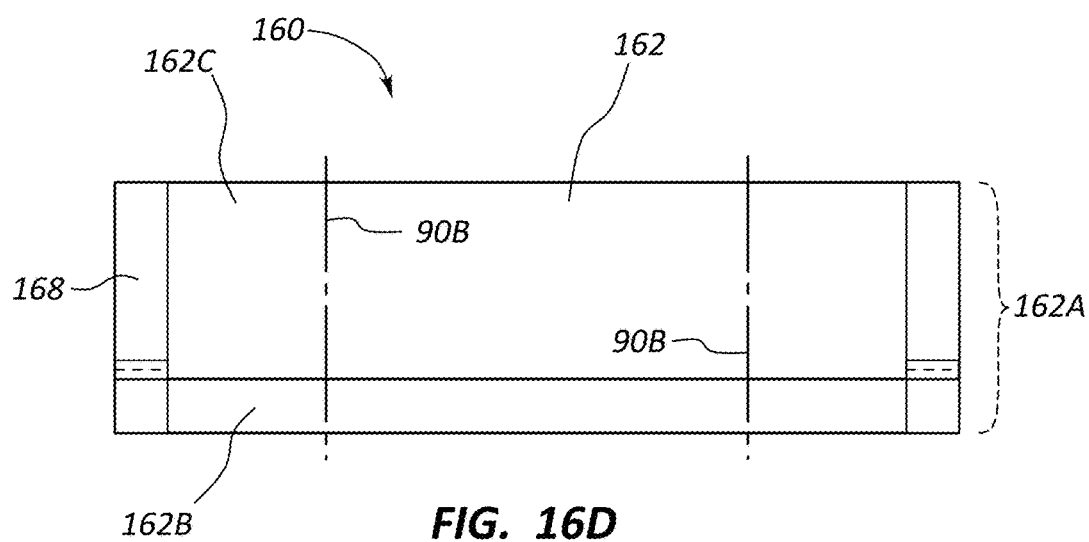
Figure 16E:
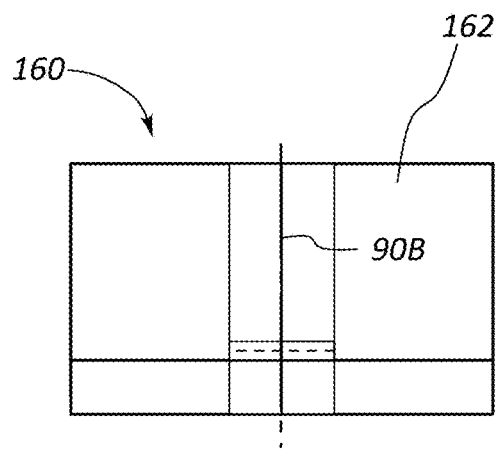
Figure 16F:
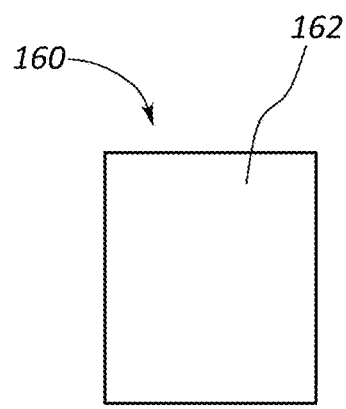

FIGS. 16D and 16E show that imaginary vertical fold lines 90B are successively used to laterally fold the wrap body 112 inward from the right end and the left end (FIG. 16D), resulting in the configuration shown in FIG. 16E. A final fold from the right end is performed (FIG. 16E). Folding in this manner produces a folded wrap assembly 160, as shown in FIG. 16F.

Figure 17A:
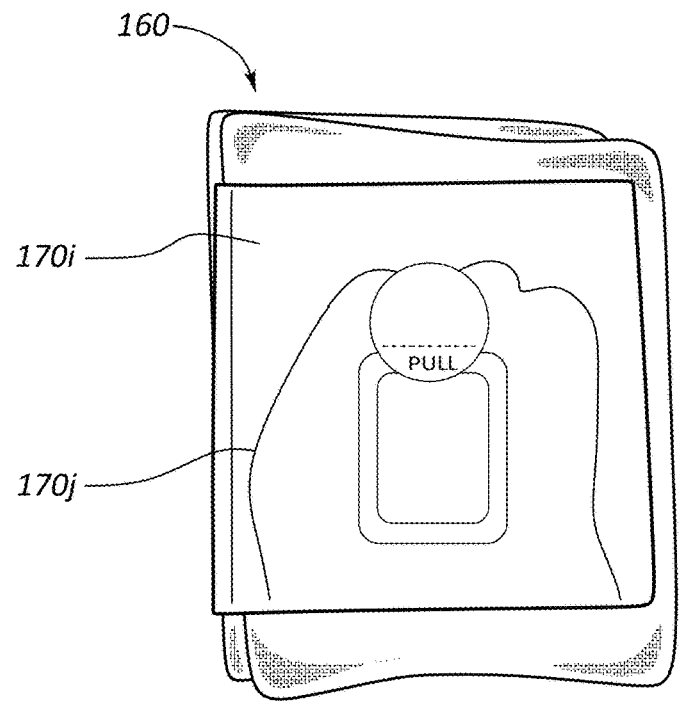
FIGS. 17A-17D depict various views of select contents of the medical device kit of FIGS. 15A and 15B.
Figure 17B:
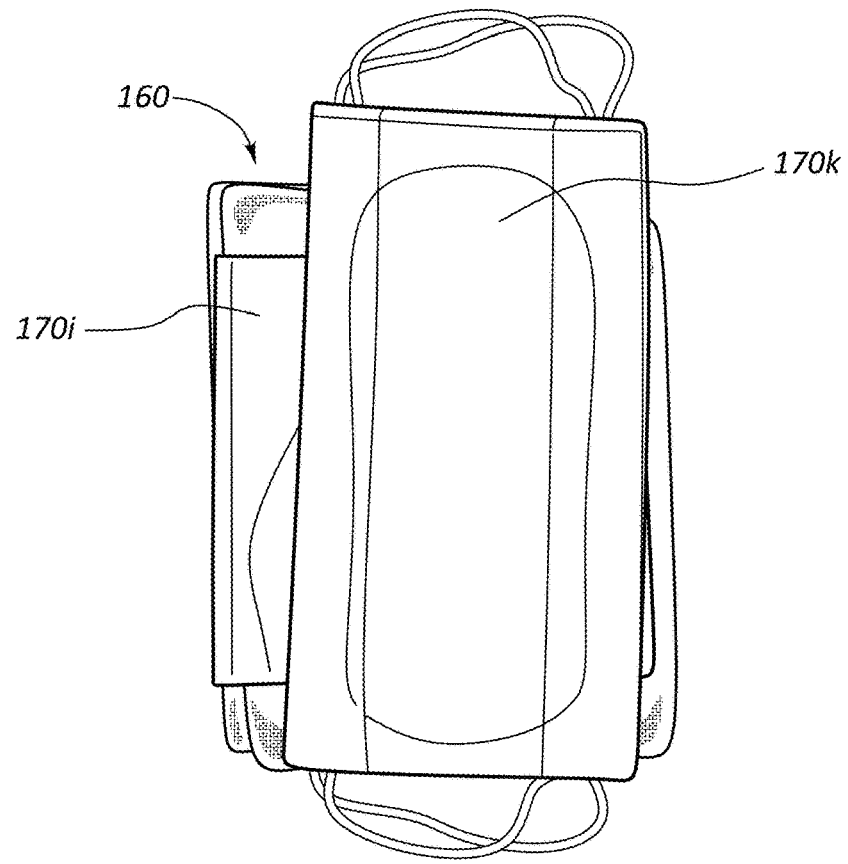
Figure 17C:
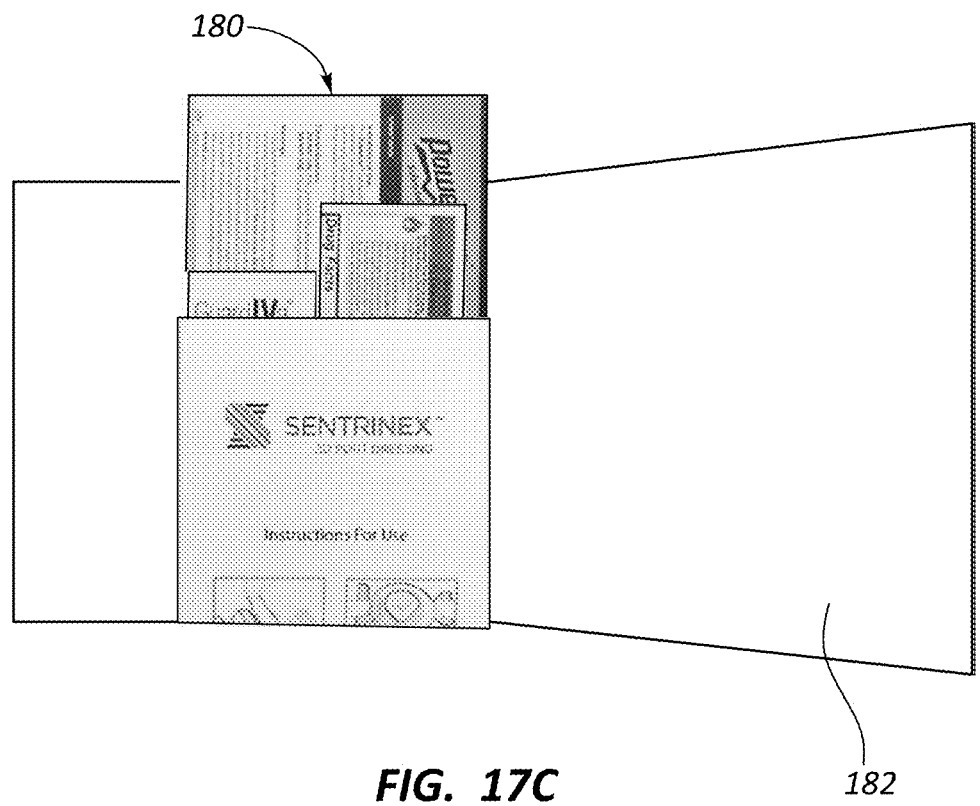
Figure 17D:
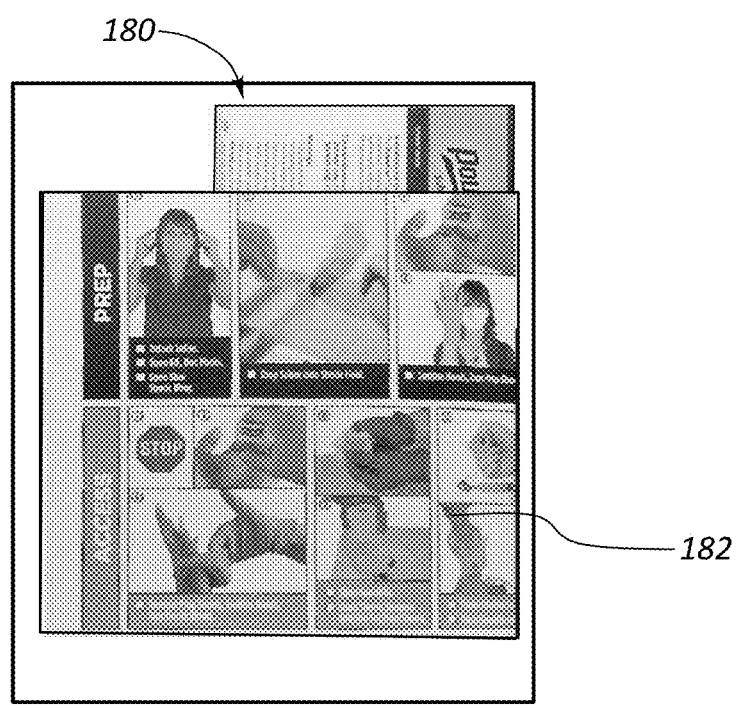
Figure 18A:
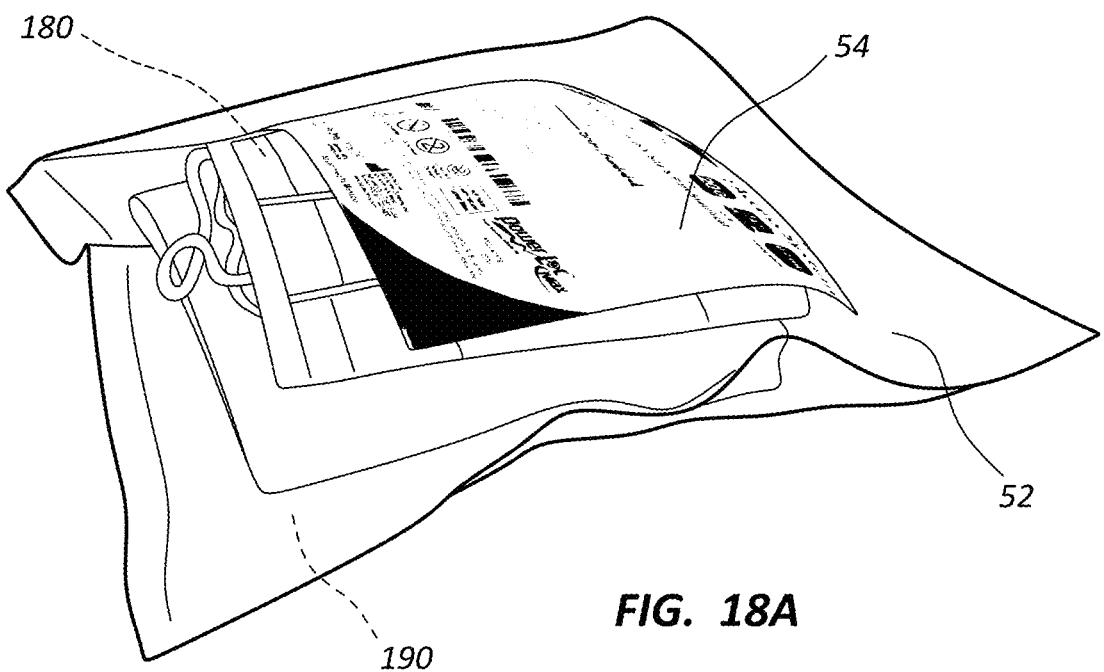
FIGS. 18A and 18B are various views of the medical device kit of FIGS. 15A and 15B.
Figure 18B:
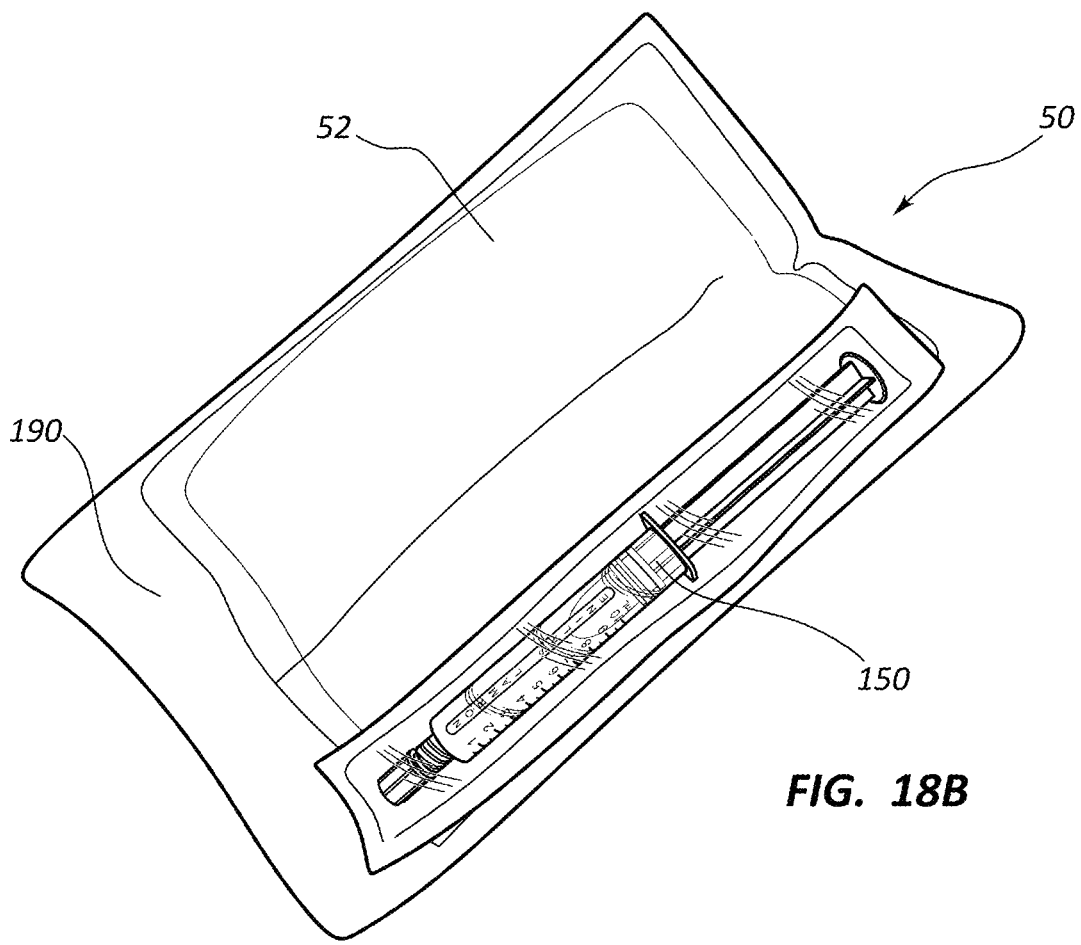

FIGS. 17A and 17B show that additional components 170, including a pair of gloves 170I, adhesively attached sanitizer packet 170I, and a pair of masks 170K, are included with the folded wrap assembly 160 prior to being inserted into the pouch 52 with documentation 180 including an instructive visual guide 182 (FIGS. 17C and 17D), as seen in FIGS. 18A and 18B. In the present embodiment, the pouch 52 includes a clear bag composed of LDPE, HDPE, and nylon and further including a TYVEK® material portion 190 (or other suitable material) to enable the pouch contents to be sterilized after sealing of the pouch is performed. As mentioned, the packaged saline syringe 150 is removably attached to the pouch 52 to complete the kit 50. In another embodiment, the saline syringe can be inserted within the pouch 52 instead of adhered to an external surface thereof.

Figure 19A:
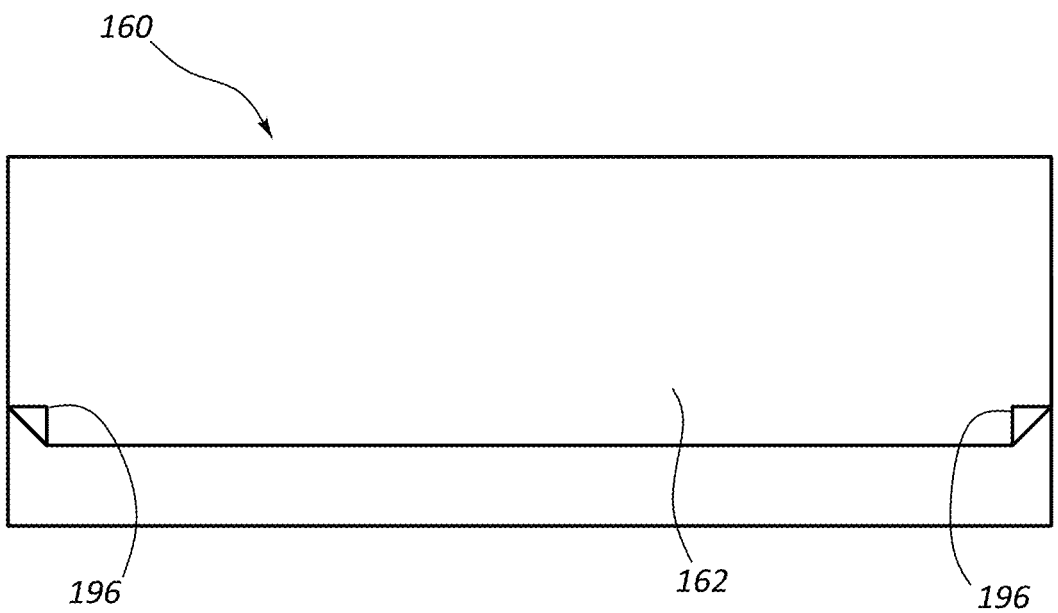
FIGS. 19A and 19B are various views of a wrap for a medical device kit according to one embodiment.
Figure 19B:
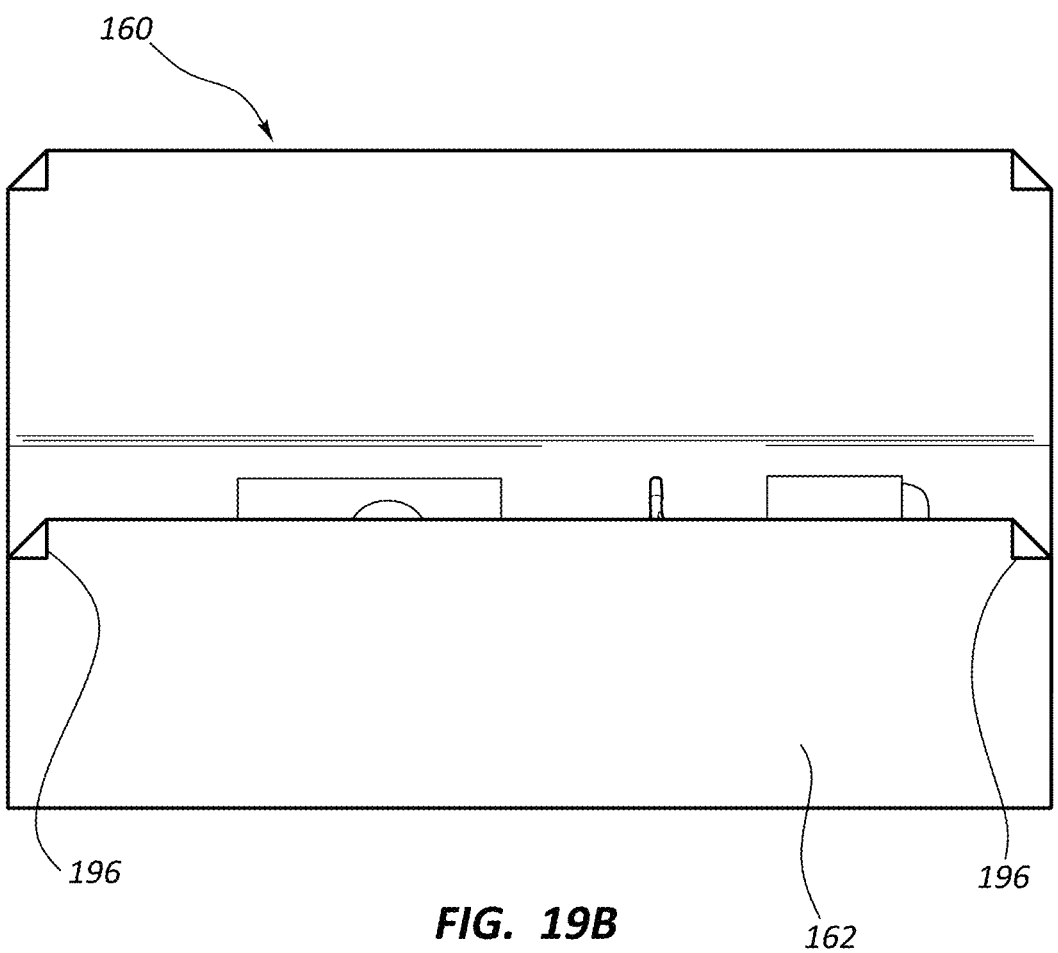

FIGS. 19A and 19B show the wrap assembly 160 according to another embodiment, wherein one, two, or more folded-up grasping tabs 196 are included on various corners of the wrap body 162 to facilitate grasping the corners during unfolding/folding of the wrap body, such as during a procedure that involves use of the wrap assembly. The size, shape, and positioning of the folded grasping tabs 196 can vary from what is shown and described herein. In another embodiment, the tabs can be separate tabs that are joined to the wrap body via adhesive or ultrasonic welding, for instance.

Figure 20:
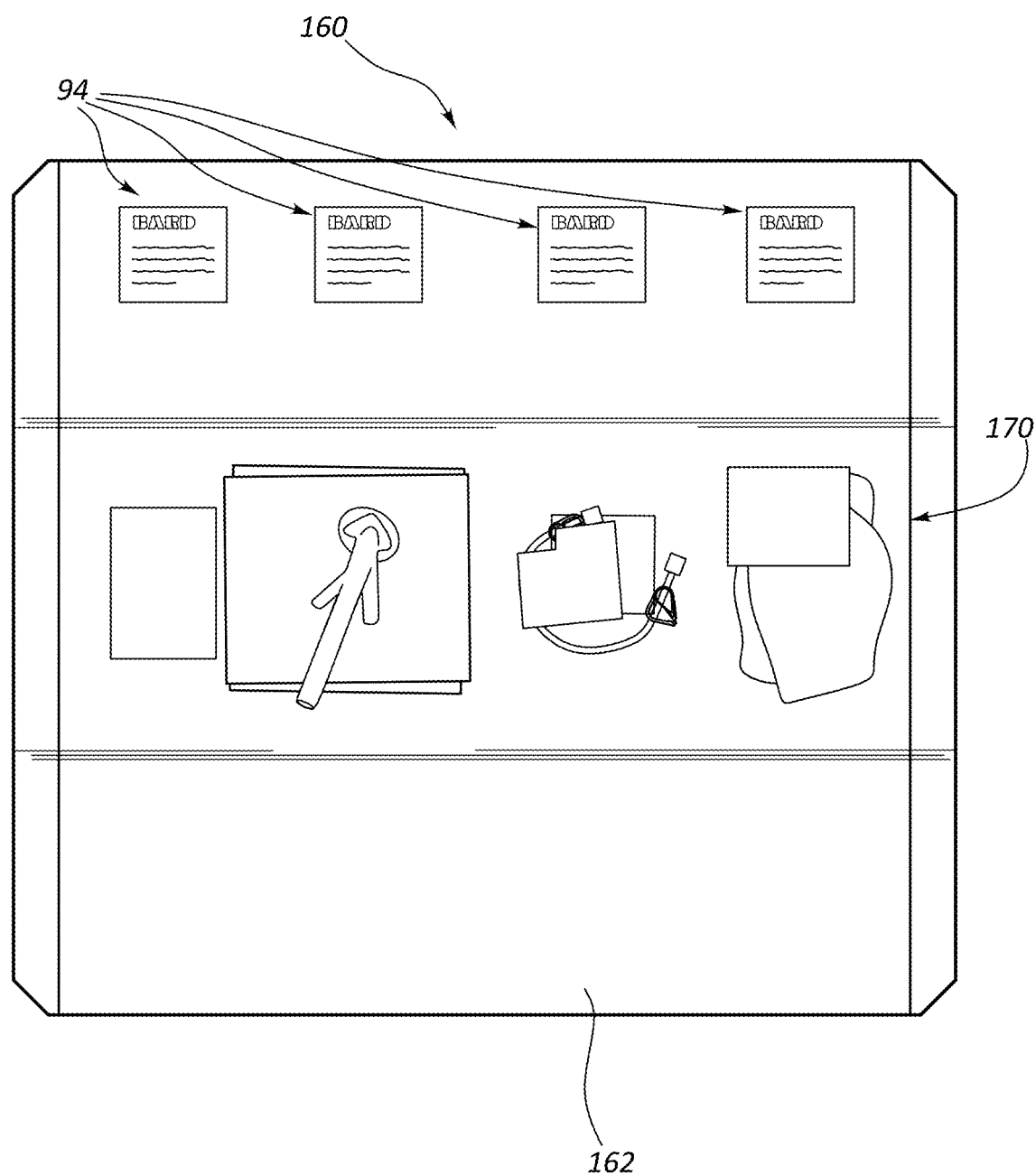
FIG. 20 is a top view of the wrap of FIGS. 19A and 19B.

FIG. 20 shows an interior portion of the wrap assembly 160, wherein the insignia 94 on the wrap body includes a plurality of printed pictures showing use of each of the corresponding components 170 included on the wrap body below the picture. This is illustrative of the variety of insignia that can be included on the wrap to assist a clinician with use of the wrap. These and other modifications are therefore contemplated.

Figure 21:
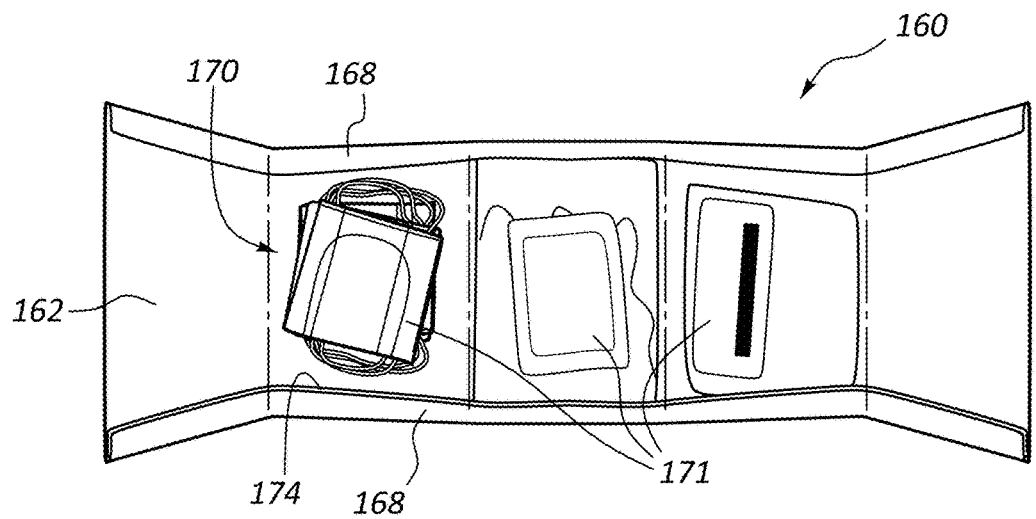
FIG. 21 is a top view of a wrap for a medical device kit according to one embodiment.

FIG. 21 depicts details of the wrap assembly 160 according to another embodiment, wherein the partially unfolded wrap body 162 includes two sterile component placement areas, including a first component placement area shown in FIG. 21 whereon various components 171 are placed in the order of use for performing a medical procedure, such as accessing a subcutaneously implanted vascular access device with an infusion set. FIG. 21 further shows that the wrap body 162 includes folded edges 168 along upper and lower borders of the wrap body in the unfolded configuration shown in FIG. 21. The folded edges 168 here are formed by creasing a portion of the upper and lower borders inward toward the center of the wrap body 162 (though other folding configurations are possible), and are configured to prevent the components 171 from sliding off the wrap body. Note that the wrap body 162 here can be folded via imaginary vertical fold lines that extend between the components 171.

Figure 22A:
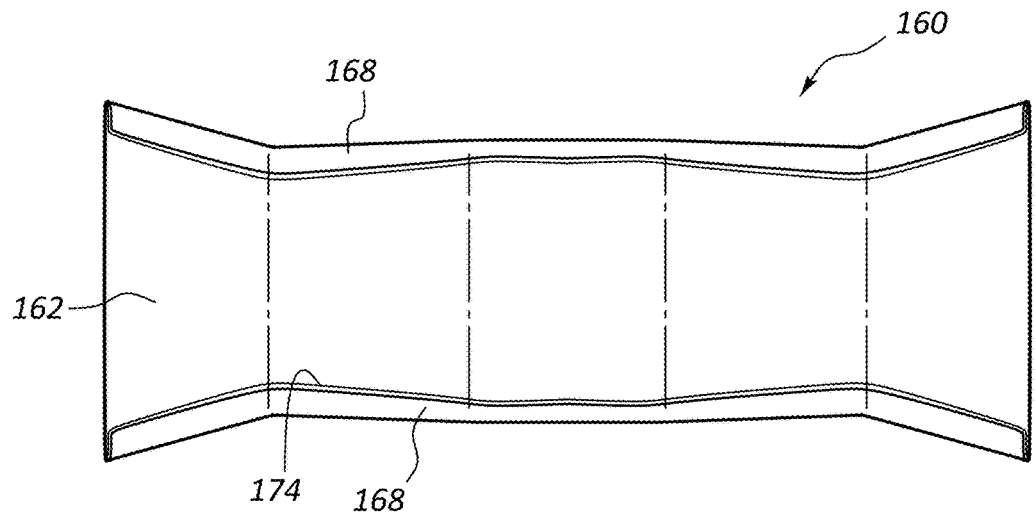
FIGS. 22A-22E depict various views of the wrap of FIG. 21.
Figure 22B:
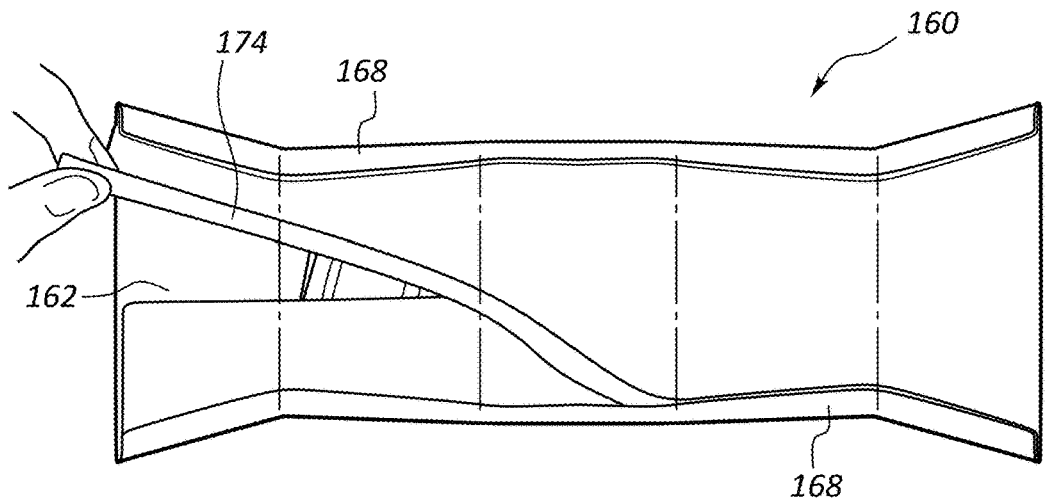
Figure 22C:
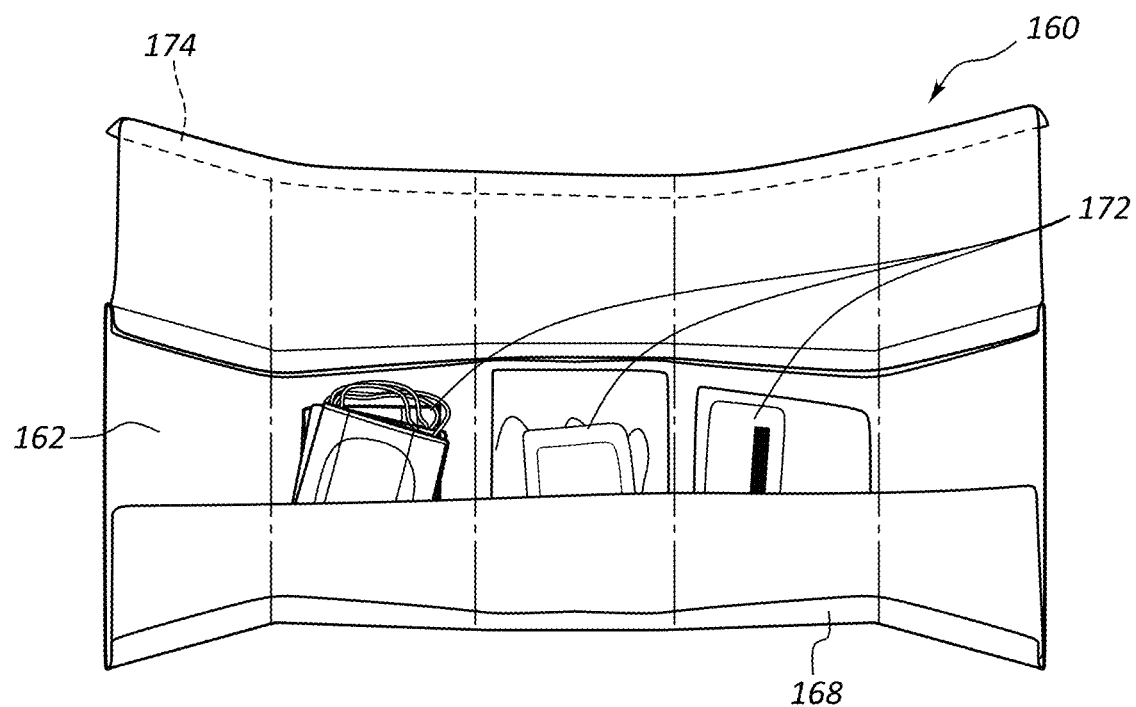
Figure 22D:
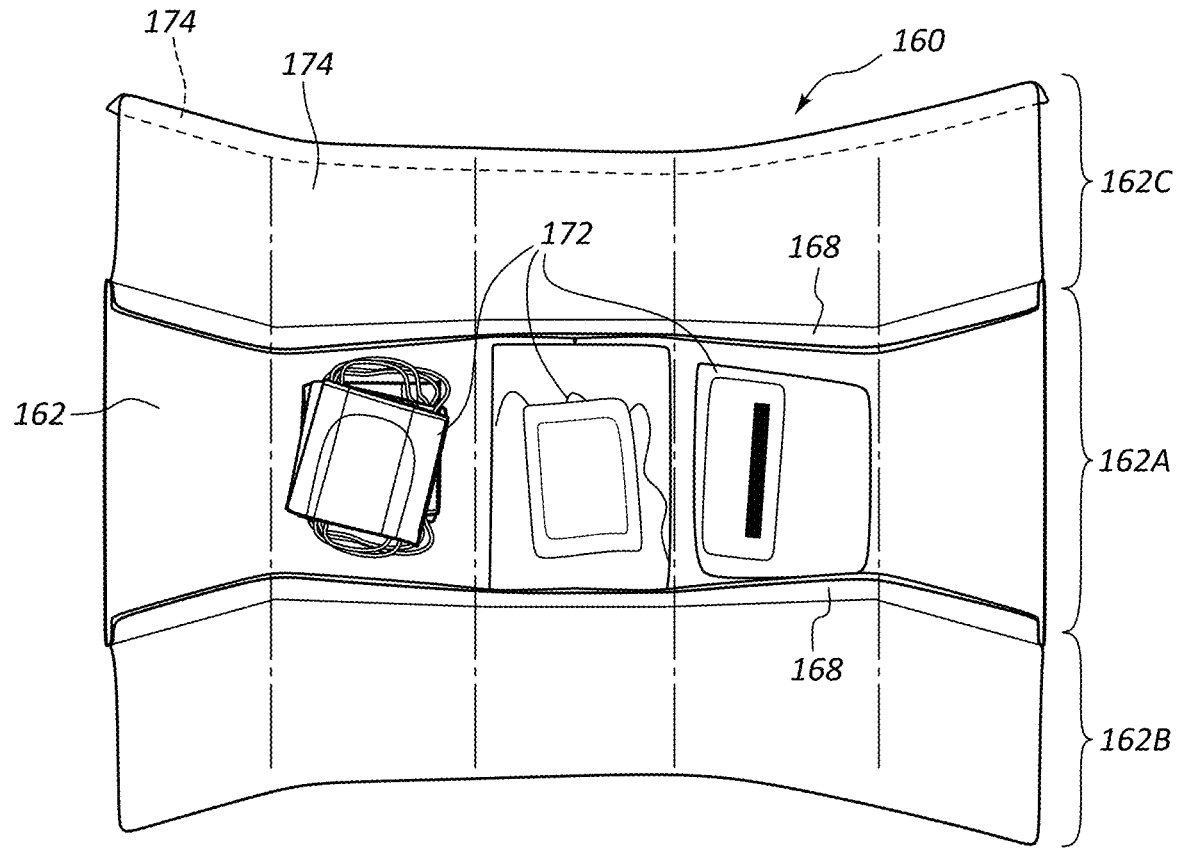
Figure 22E:
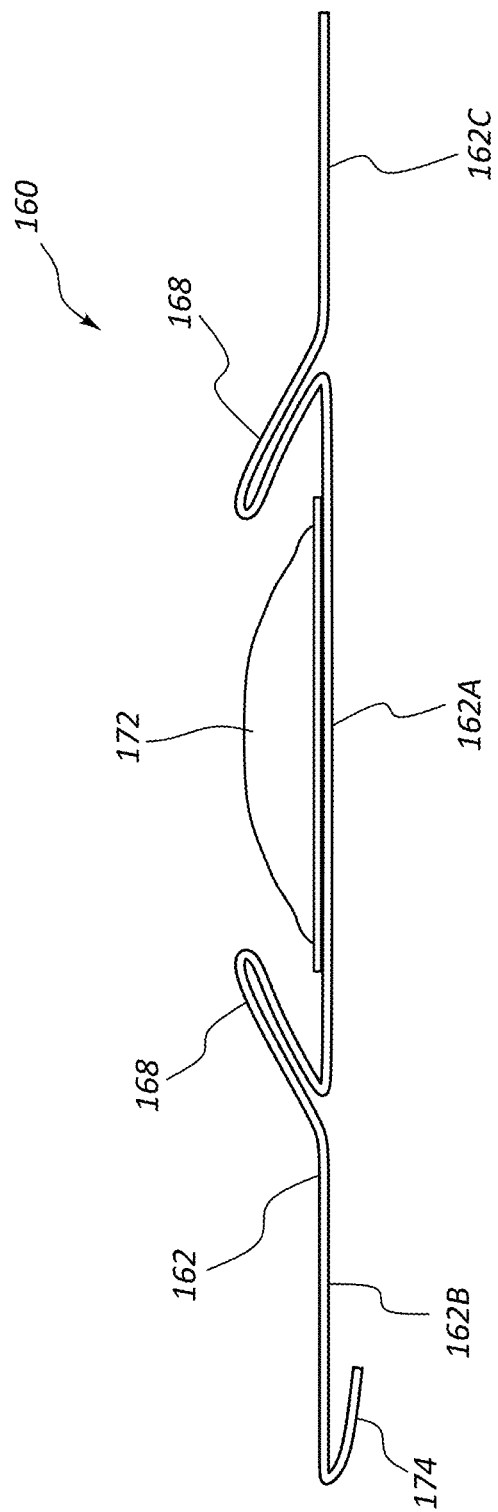

FIGS. 22A and 22B show details of further unfolding of the wrap assembly 160 from that shown in FIG. 21, after the top components 171 have been removed. As shown in FIGS. 22A and 22B, a top edge 174 of the wrap body 162 is folded along its length to enable a clinician to grasp it and lift a top portion 162C of the wrap body to reveal an intermediate portion 162B and a bottom portion 162A of the wrap body, as shown in FIG. 22C. The intermediate portion 162B of the wrap body 162 can then be pulled back to reveal one or more interior components 172 disposed on a second component placement area on a front surface of the bottom portion 162A of the wrap body, as shown in FIG. 22D. FIG. 22E, which gives a side view of the unfolded wrap body 162, shows that the intermediate portion 162B and the top portion 162C of the wrap body 162 do not fully extend when unfolded, but are creased to provide a folded edge about the top and bottom edges of the bottom portion 162A so as to assist with preventing the components 172 from falling off the second component placement area.

Figure 23A:
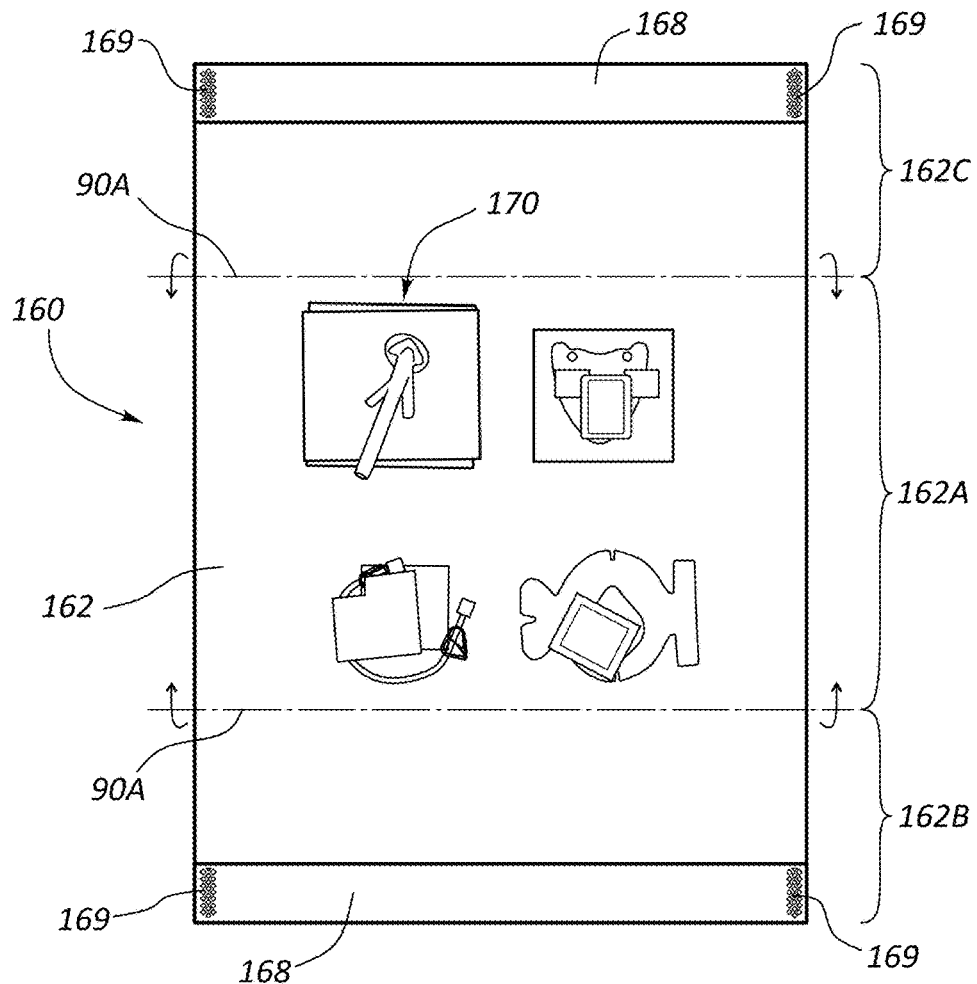
FIGS. 23A-23D depict various views of a wrap for a medical device kit according to one embodiment.
Figure 23B:
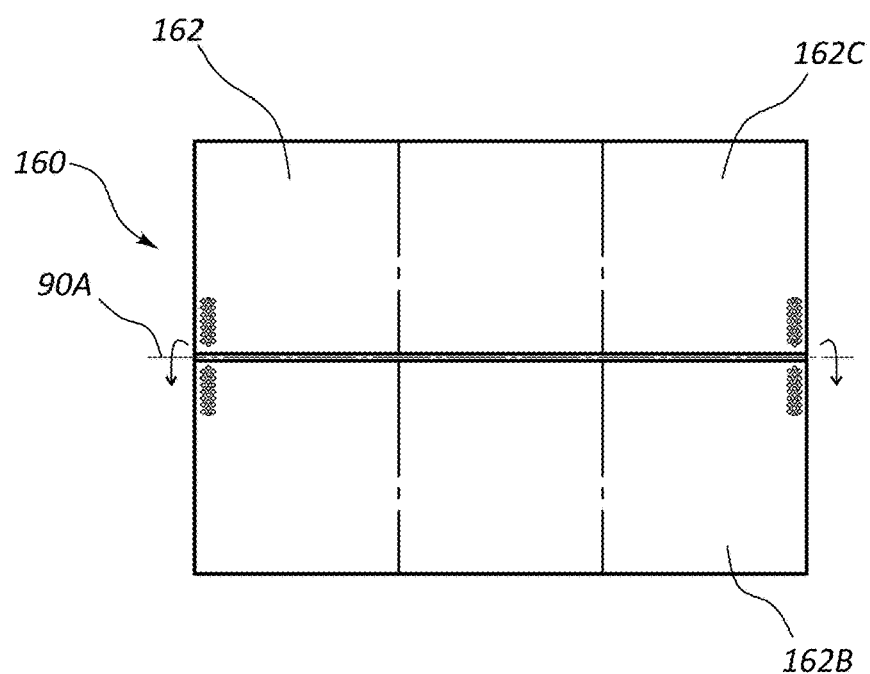
Figure 23C:
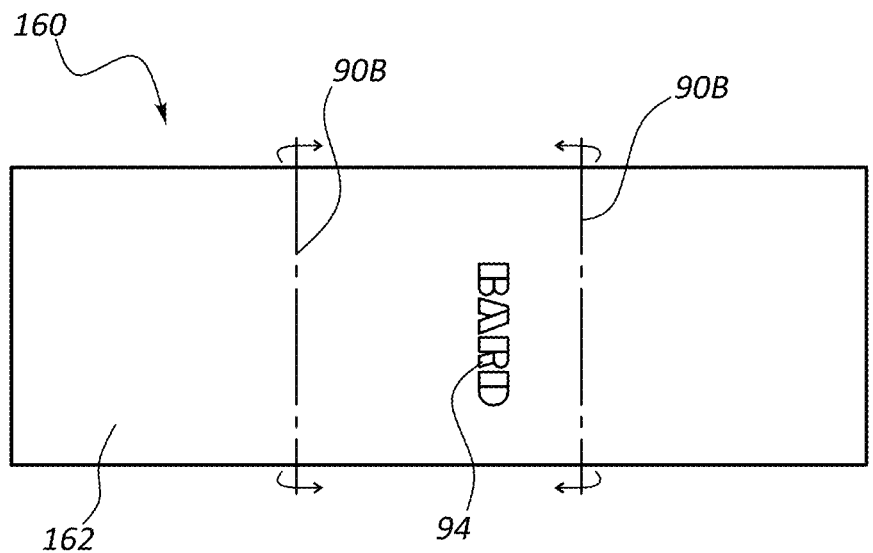
Figure 23D:
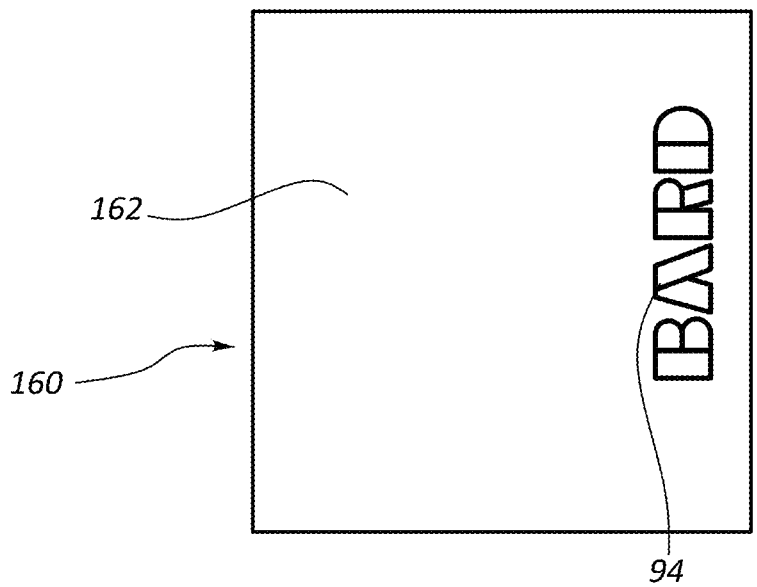

FIG. 23A depicts details of the wrap assembly 160 according to another embodiment, wherein the unfolded wrap body 162 includes the component placement area on the bottom portion of the wrap body, with the components placed in a square pattern. The folded edges 168 with corresponding weld points are also included at the top and bottom of the wrap body 162. Two lateral fold lines 90A are shown along which the wrap body 162 can be folded so as to bring the intermediate portion 162B and the top portion 162C together to meet in the middle atop the bottom portion 162A, as shown in FIG. 23B. Another lateral folding along the interface of the intermediate portion 162B and the top portion 162C produces the configuration shown in FIG. 23C, before folding along the two vertical fold lines 90B results in the folded wrap body configuration shown in FIG. 23D. The wrap assembly 160 can then be packaged, such as in a pouch of a kit, for instance.

Figure 24:
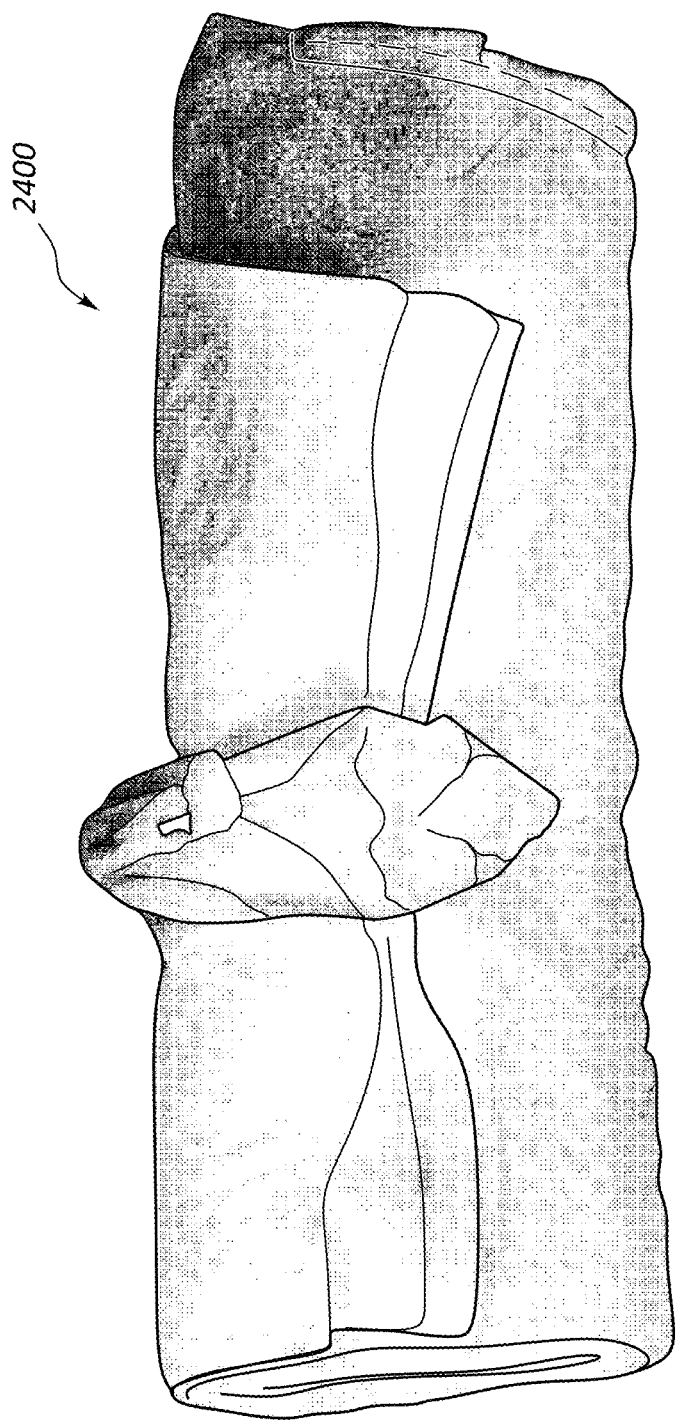
FIG. 24 provides a view of a rolled wrap assembly of a medical device kit according to some embodiments.

FIG. 24 provides a view of a rolled wrap assembly 2400 of a medical device kit according to some embodiments.

The rolled wrap assembly 2400 can be disposed in a pouch such as, but not limited to, the pouch 52 described in association with the medical device kit 50 shown in FIG. 2. The pouch can include a label such as the label 54 to identify the medical device kit. In some embodiments, the medical device kit can be a urinary catheterization kit including the rolled wrap assembly 2400 in a pouch with a label identifying the urinary catheterization kit.

Figure 25:
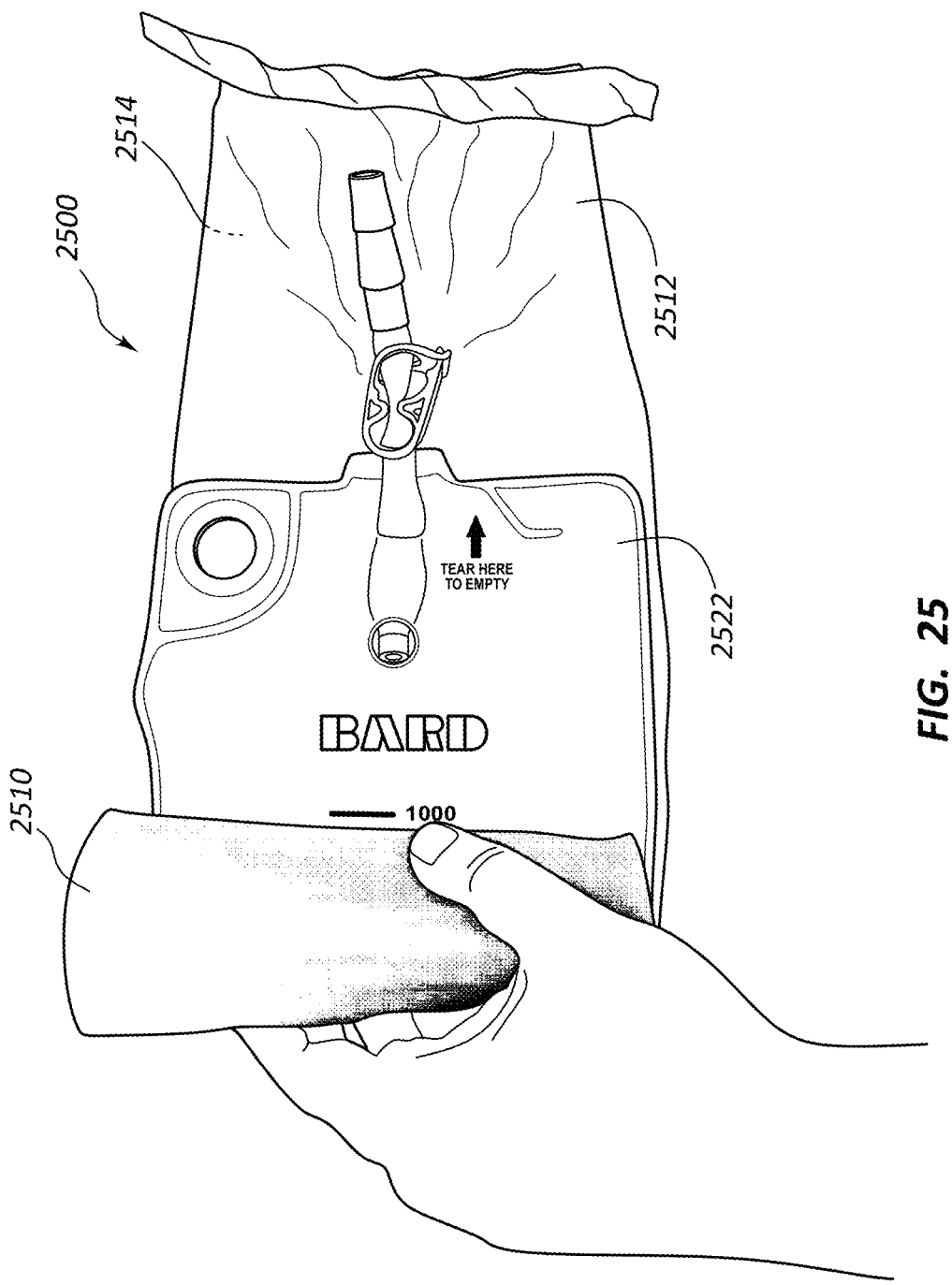
FIG. 25 provides a view of a partially unrolled wrap assembly of a medical device kit according to some embodiments.

FIG. 25 provides a view of a partially unrolled wrap assembly 2500 of a medical device kit according to some embodiments.

As shown, the partially unrolled wrap assembly 2500 includes a wrap body 2510, which includes a front surface 2512 and a back surface 2514 of the wrap body 2510. The wrap body 2510 can be of any material suitable for a medical device kit including, but not limited to, a woven fabric, a nonwoven fabric such as the SMS nonwoven fabric described in association with the wrap assembly 60 of FIG. 3A, or central supply room ("CSR") wrap. Because the CSR wrap is a sterilizable material, a wrap body of CSR wrap can be easily sterilized in accordance with the gas sterilization procedure described in association with FIGS. 11A and 11B.

When the medical device kit is a urinary catheterization kit, the wrap body 2510 can be configured to roll up around catheterization components of the urinary catheterization kit. As shown in FIG. 25, the urinary catheterization kit can include at least a drainage bag 2522 as part of the catheterization components. The urinary catheterization kit can be configured for placement of the drainage bag 2522 over the front surface 2512 of the wrap body 2510 (and over the pockets 2616 of FIG. 26A) to sandwich at least some of the other catheterization components between the drainage bag 2522 and the wrap body 2510. As such, a combination of the drainage bag 2522 and the wrap body 2510 can be configured to roll up around the other catheterization components to form the wrap assembly 2400 of the urinary catheterization kit. The combination of the drainage bag 2522 and the wrap body 2510 can add structural integrity to the wrap assembly 2400 compared to simply rolling or folding the drainage bag 2522 and placing it in the wrap assembly 2400.

Figure 26A:
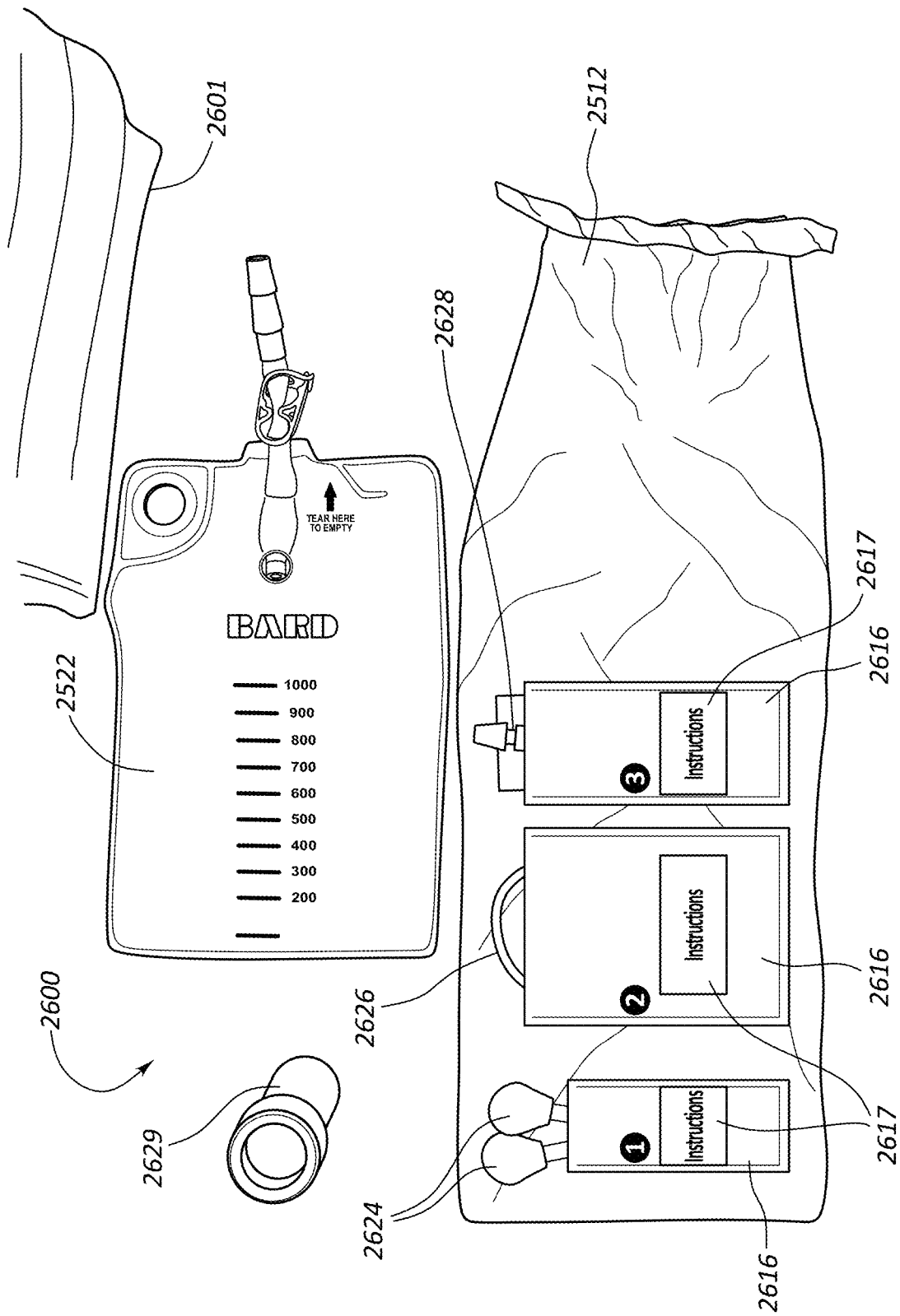
FIG. 26A provides a view of a fully unrolled wrap assembly of a medical device kit according to some embodiments.

Following on the foregoing, the catheterization components can further include at least a specimen container 2629 as shown in FIG. 26A. The urinary catheterization kit can be further configured for placement of the specimen container 2629 over the drainage bag 2522 when the drainage bag 2522 is placed over the front surface 2512 of the wrap body 2510 (and over the pockets 2616 of FIG. 26A). The combination of the drainage bag 2522 and the wrap body 2510 can be configured to roll up around the specimen container 2629 adding additional structural integrity to the wrap assembly 2400. In other words, the urinary catheterization kit can be further configured for placement of the specimen container 2629 in a center of a combined roll of the drainage bag 2522 and the wrap body 2510.

Figure 26B:
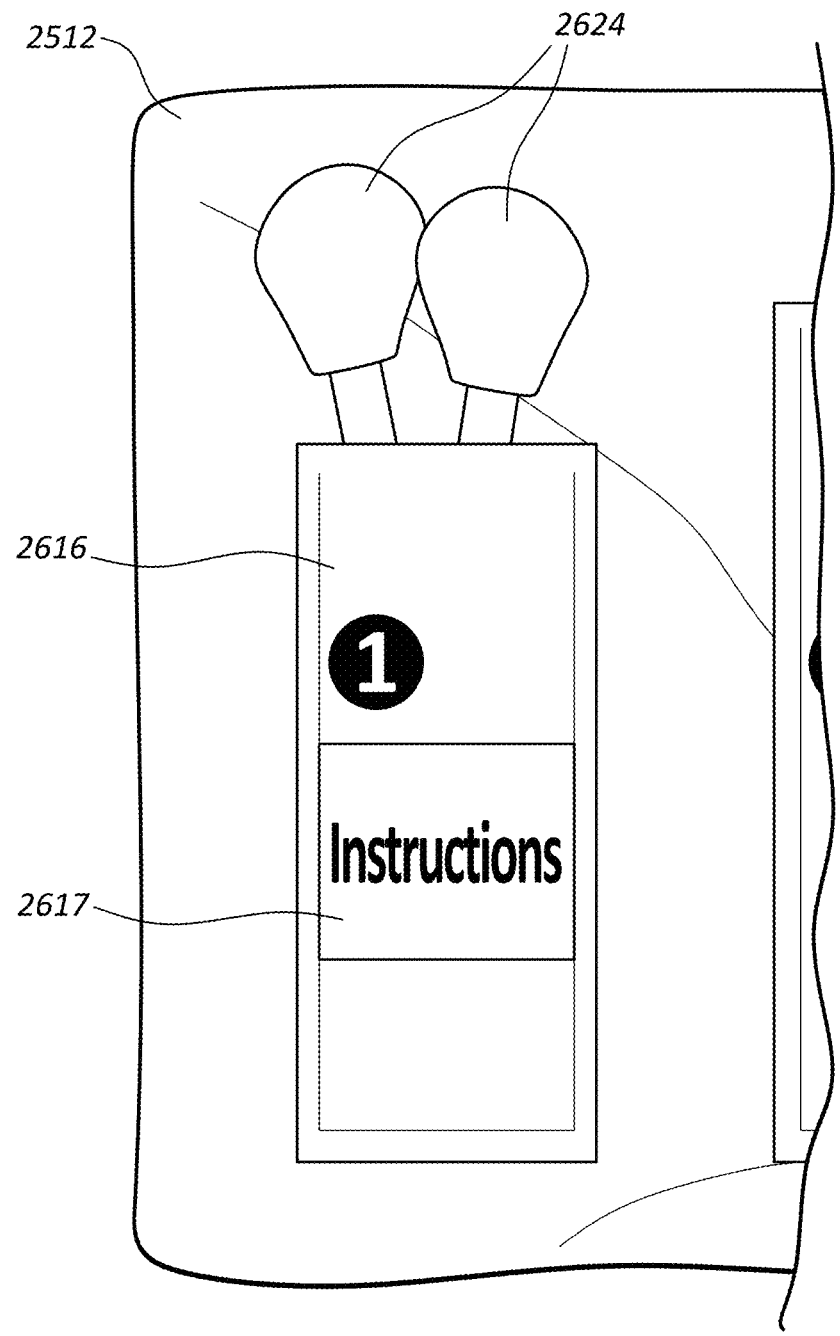
FIG. 26B provides a close-up view of a first pocket of the fully unrolled wrap assembly of FIG. 26A according to some embodiments.
Figure 26C:
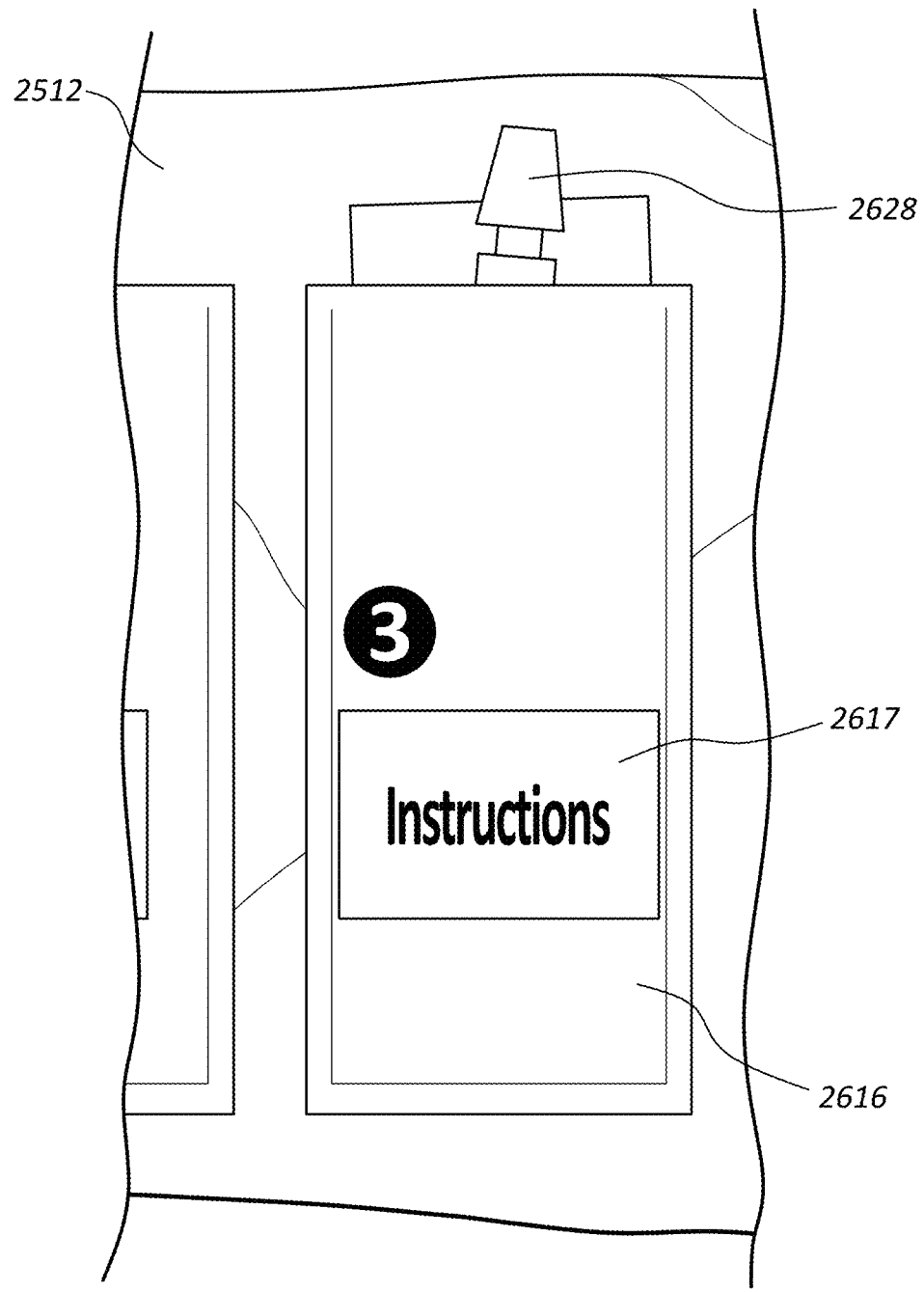
FIG. 26C provides a close-up view of a second pocket of the fully unrolled wrap assembly of FIG. 26A according to some embodiments.

FIG. 26A provides a view of a fully unrolled wrap assembly 2600 of a medical device kit according to some embodiments. FIG. 26B provides a close-up view of a first pocket of the fully unrolled wrap assembly 2600, while FIG. 26C provides a close-up view of a second pocket of the fully unrolled wrap assembly 2600.

As shown, the fully unrolled wrap assembly 2600 exposes an entirety of the front surface 2512 of the wrap body 2510, which front surface 2512 can be configured to define at least an aseptic field. However, the gas sterilization procedure described in association with FIGS. 11A and 11B can further provide a sterile field for a medical procedure such as the example urinary catheterization procedure.

The front surface 2512 of the wrap body 2510 can be further configured to include a number of pockets 2616 for components of the medical device kit such as the catheterization components of the urinary catheterization kit shown in FIG. 26A. The pockets 2616 can be configured to accommodate the catheterization components in accordance with a predetermined order of use in a stepwise system for a urinary catheterization procedure. In this way, the aseptic or sterile filed is not compromised as the clinician performing the urinary catheterization procedure or a user performing a self-catheterization procedure works across the fully unrolled wrap assembly 2600 (e.g., works from left to right across the fully unrolled wrap assembly 2600).

The catheterization components of the urinary catheterization kit can be selected from, but are not limited to, one or more pairs of gloves; an underpad; a perineal care kit such one or more perineal wipes to cleanse at least a portion of the patient's or user's or perineum prior to catheterization; hand sanitizer; lubricant in a package or a container such as a syringe for lubricating the catheter; an antiseptic such as an iodophor (e.g., povidone-iodine, tincture of iodine, aqueous iodine, etc.); swabs or swab sticks for use with the antiseptic; a urinary catheter such as an intermittent catheter; drainage tubing; a drainage bag; and a specimen container. The urinary catheterization kit shown in FIG. 26A is an example of an intermittent catheter kit including a drainage bag 2522; swab sticks 2624; drainage tubing 2626; lubricant 2628; and a specimen container 2629. The catheterization components can be arranged in the pockets 2616 of the wrap body 2510 in a predetermined order of use, which, in combination with instructions 2617, provides the stepwise system for the urinary catheterization procedure.

Instructions 2617 for using the urinary catheterization kit or performing the urinary catheterization procedure are included on the number of pockets 2616 in FIG. 26A; however, the instructions 2617 can be alternatively or additionally included on the front surface 2512 of the wrap body 2510. That is, the instructions 2617 can be printed, presented, or otherwise provided on the front surface 2512 of the wrap body 2510, the pockets 2616 thereof, or a combination thereof. Some of the instructions 2617 can even be printed on a packaging label identifying the catheterization package and emphasizing key features of the catheterization package. The instructions 2617 can include text, graphics, or a combination thereof, and the instructions 2617 can be presented in accordance with the catheterization components arranged in the pockets 2616 of the wrap body 2510 in the predetermined order of use providing the stepwise system for the urinary catheterization procedure. For example, if a first step in a urinary catheterization procedure for self-catheterization with an intermittent catheter is to don clean gloves, then the clean gloves can be in a first pocket of the pockets 2616, and the instructions 2617 associated with the first step can be written on or around the first pocket. If a second step in the urinary catheterization procedure is to clean one's perineum, then the one or more perineal wipes can be in either the first pocket or a second pocket of the pockets 2616, and the instructions 2617 associated with the second step can be written on or around the first or second pocket.

Removal of at least some of the catheterization components from the pockets 2617 can reveal instructions hidden by those catheterization components prior to their removal. Following on the foregoing first and second steps, for example, removal of the gloves from the first pocket in the first step can reveal perineal cleaning instructions for the second step, wherein the perineal cleaning instructions are on the front surface 2512 of the wrap body 2510 and were initially hidden by the gloves in the first pocket. The instructions revealed by the removal of those catheterization components are further part of the stepwise system for the urinary catheterization procedure.

A pouch 2601 is further shown in FIG. 26A. Again, the rolled wrap assembly 2400 can be disposed in such a pouch to provide a medical device kit, in this case, the urinary catheterization kit. While the pouch can include a label to identify the medical device kit, it can also include some instructions as part of the stepwise system for the urinary catheterization kit.

Figure 27:
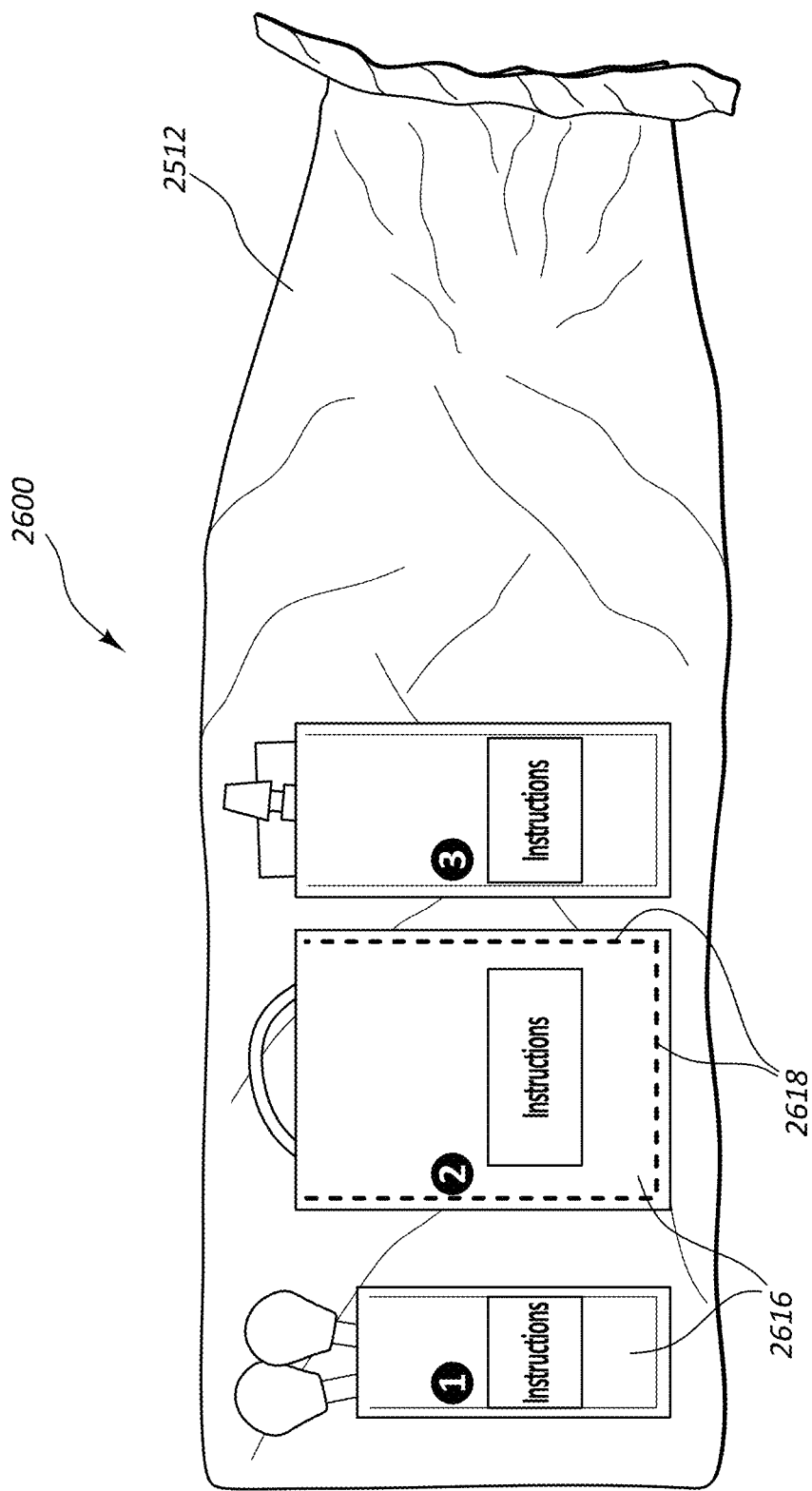
FIG. 27 provides another view of a fully unrolled wrap assembly of a medical device kit according to some embodiments.

FIG. 27 provides a view of a fully unrolled wrap assembly of a medical device kit according to some embodiments.

Again, as shown, the fully unrolled wrap assembly 2600 exposes an entirety of the front surface 2512 of the wrap body 2510, which front surface 2512 includes a number of pockets 2616 for the catheterization components.

The pockets 2616 can be formed from any combination of one or more pieces of a same or different material than the wrap body 2510. For example, the pockets 2616 can be formed from the same sterilizable material (e.g., CSR wrap) as the wrap body 2510, which can be advantageous with respect to joining together similar materials as opposed to joining together dissimilar materials having different properties and requirements. Whether the pockets 2616 are formed from one or more pieces of the same or different material than the wrap body 2510, the one or more pieces of the material can be adhered with a suitable adhesive to the wrap body 2510, ultrasonically welded to the wrap body 251, or a combination thereof. With the adhesive, adhesive beads along the bottoms of the pockets 2616 form bottom seams of the pockets 2616, and adhesive beads along the sides of the pockets 2616 form the side seams of the pockets 2616. Likewise, with the ultrasonic welding, ultrasonic welds along the bottoms of the pockets 2616 form the bottom seams of pockets 2616, and ultrasonic welds along the sides of the pockets 2616 form the side seams of the pockets 2616. Such seams are shown in FIG. 27 as seams 2618.

While FIG. 27 is shown with one piece of material (e.g., CSR wrap) per pocket of the pockets 2616, it should be understood that any two or more of the pockets 2616 can be formed from just a single piece of the material. For example, a single adhesive bead along a bottom of the one piece of material can form the bottom seams of the two or more pockets, while the side seams of the two or more pockets can be formed by adhesive beads at both ends of the one piece of material and an additional adhesive bead in a medial portion of the one piece of material for every two pockets of the two or more pockets.

A urinary catheterization kit as set forth herein can be manufactured in a number of steps including, but not limited to, forming a wrap body for the urinary catheterization kit; forming a plurality of pockets on the wrap body; printing instructions on the wrap body, the pockets, or a combination thereof; filling the pockets with catheterization components; rolling the wrap body around the catheterization components to form the urinary catheterization kit. An additional step can include sterilizing the urinary catheterization kit.

Forming the wrap body can include, but is not limited to, cutting the wrap body to size from a stock material such as a sterilizable stock material (e.g., CSR wrap). The wrap body can include a front surface, wherein the front surface is configured to provide at least an aseptic field to a clinician or a user of the urinary catheterization kit.

Forming the plurality of pockets on the wrap can include, but is not limited to, forming the pockets on the front surface of the wrap body. The pockets can be formed of one or more pieces of a same or different stock material than the wrap body. For example, the same sterilizable stock material as the wrap body can be cut into one or more pieces for the pockets. With the one or more pieces, the pockets can be further formed by adhering or welding the one or more pieces to the wrap body. With respect to adhering the one or more pieces to the wrap body, one or more adhesive beads can define bottoms and sides of the pockets. With respect to welding the one or more pieces to the wrap body, one or more ultrasonic welds can define bottoms and sides of the pockets.

Printing the instructions on the wrap body, the pockets, or the combination thereof can include, but is not limited to, printing instructions including text, graphics, or both text and graphics on the front surface of the wrap body, the pockets, or the combination thereof. Printing the instructions can include presenting the instructions with a predetermined order of steps in accordance with a stepwise system for a urinary catheterization procedure. Some of the instructions can be printed on the front surface of the wrap body such that the instructions are hidden by the catheterization components when the catheterization components are arranged in the pockets per the stepwise system for the urinary catheterization procedure. In this way, such hidden instructions are revealed, as needed, when certain catheterization components are removed from the urinary catheterization kit.

Filling the pockets with the catheterization components can include, but is not limited to, arranging the catheterization components in the pockets for subsequent removal of the catheterization components according to the stepwise system for the urinary catheterization procedure. The catheterization components for the arranging can be selected from, but are not limited to, one or more pairs of gloves, an underpad, one or more perineal wipes, hand sanitizer, lubricant, an antiseptic, swab sticks, a urinary catheter (e.g., intermittent catheter), drainage tubing, a drainage bag, and a specimen container.

Rolling the wrap body around the catheterization components can include first placing a drainage bag over the pockets to sandwich at least some other catheterization components in the pockets between the drainage bag and the wrap body. Rolling the wrap body around the catheterization components then includes rolling a combination of the drainage bag and the wrap body around the at least some other catheterization components to form the urinary catheterization kit.

Following on the foregoing, rolling the wrap body around the catheterization components can further include placing a specimen container over the drainage bag. Rolling the wrap body around the catheterization components then includes rolling the combination of the drainage bag and the wrap body around the specimen container and the at least some other catheterization components to form the urinary catheterization kit.

Sterilizing the urinary catheterization kit can include sterilizing the urinary catheterization kit in accordance with sterilization methods set forth herein for other medical device kits. For example, the urinary catheterization kit can be disposed in a pouch of LDPE, HDPE, nylon, TYVEK®, or the like and sterilized via gas sterilization. Sterilizing the urinary catheterization kit provides at least an aseptic field over the front surface of the wrap body upon unrolling the urinary catheterization kit.

A urinary catheterization kit as set forth herein can be used by a clinician (on a patient) or a user (on himself or herself) in a number of steps including, but not limited to, removing the urinary catheterization kit from a pouch (if present); unrolling the urinary catheterization kit on a surface; and following instructions of the urinary catheterization kit for a urinary catheterization procedure. Unrolling the urinary catheterization kit includes revealing i) a front surface of a wrap body defining at least an aseptic field for the urinary catheterization procedure, ii) a plurality of pockets including an arrangement of catheterization components, and iii) the instructions on the front surface, the pockets, or a combination thereof for performing the urinary catheterization procedure. Some of the instructions might only be revealed when certain catheterization components are removed from their respective pockets. Following the instructions includes following the predetermined order of steps presented in the instructions, which includes removing and using the catheterization components in accordance with a stepwise system for the urinary catheterization procedure.

In view of the foregoing, medical devices kits such as the urinary catheterization kit set forth herein including the wrap assembly 2400 in the pouch 2601 provide a compact, environmentally friendly, tray-free design for medical device kits. The pockets 2616 on the wrap body 2400, as well as the instructions 2717 provided on the wrap body 2400, the pockets 2616, or the combination thereof eliminates any need for a tray. Not only does elimination of trays provide an environmental benefit, but manufacturing costs are reduced as well in comparison to manufacturing, for example, thermoformed trays. Furthermore the step-by-step instructions (e.g., for self-catheterization with an intermittent catheter) of the medical device kits are presented in a user friendly, intuitive manner that aids in and ensures aseptic techniques.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A method of using a urinary catheterization kit, comprising:
    removing a wrap assembly in a rolled configuration from a pouch;
    unrolling the wrap assembly from the rolled configuration to an unrolled configuration, the wrap assembly comprising:
        a wrap body including a front surface defining an aseptic field for a urinary catheterization procedure;
        a plurality of pockets on the front surface;
        urinary catheterization components disposed in the plurality of pockets, the urinary catheterization components arranged in a predetermined order of use for the urinary catheterization procedure;
        printed instructions on the front surface, the plurality of pockets, or a combination thereof, the printed instructions presented in the predetermined order of use for the urinary catheterization procedure;
        a drainage bag over the plurality of pockets and the urinary catheterization components; and
        a specimen container on the drainage bag;
    removing the specimen container and the drainage bag from the wrap assembly; and
    performing the urinary catheterization procedure according to the printed instructions.

2. The method according to claim 1, wherein the drainage bag completely covers the plurality of pockets and the urinary catheterization components in the unrolled configuration.

3. The method according to claim 1, wherein the plurality of pockets are ultrasonically welded onto the front surface.

4. The method according to claim 1, wherein the wrap body is formed solely from central supply room (CSR) wrap material.

5. The method according to claim 1, wherein performing the urinary catheterization procedure comprises working in a stepwise left to right manner to maintain sterility of the urinary catheterization components.

6. The method according to claim 5, wherein the front surface of the wrap body includes printed instructions on an inside of one or more of the plurality of pockets, the printed instructions initially covered by one or more of the urinary catheterization components the one or more of the plurality of pockets.

7. The method according to claim 5, wherein the pouch includes a label to identify the urinary catheterization kit and instructions pertaining to the stepwise left to right manner.

8. The method according to claim 1, wherein the urinary catheterization components include one or more pair of gloves, an underpad, a perineal care kit, hand sanitizer, lubricant in a syringe, an iodophor antiseptic, one or more swab sticks, and a urinary intermittent catheter.

* * * * *